United States Patent
Jana et al.

(10) Patent No.: US 10,195,022 B2
(45) Date of Patent: Feb. 5, 2019

(54) NANOFIBROUS BIOLOGIC HEART VALVE LEAFLETS AND FIBROSA LAYER OF A LEAFLET

(71) Applicant: Mayo Foundation for Medical Education and Research, Rochester, MN (US)

(72) Inventors: Soumen Jana, Rochester, MN (US); Amir Lerman, Rochester, MN (US); Robert D. Simari, Mission Hills, KS (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 48 days.

(21) Appl. No.: 15/096,478

(22) Filed: Apr. 12, 2016

(65) Prior Publication Data
US 2016/0317295 A1 Nov. 3, 2016

Related U.S. Application Data

(60) Provisional application No. 62/154,880, filed on Apr. 30, 2015.

(51) Int. Cl.
*A61F 2/24* (2006.01)
*A61L 27/38* (2006.01)
*A61L 27/36* (2006.01)

(52) U.S. Cl.
CPC .......... *A61F 2/2415* (2013.01); *A61L 27/367* (2013.01); *A61L 27/3691* (2013.01); *A61L 27/3804* (2013.01); *A61L 27/3895* (2013.01); *A61F 2/2412* (2013.01); *A61F 2210/0076* (2013.01); *A61F 2310/00365* (2013.01); *A61F 2310/00371* (2013.01); *A61L 2400/12* (2013.01); *A61L 2430/20* (2013.01)

(58) Field of Classification Search
CPC ........................................................ A61F 2/24
See application file for complete search history.

(56) References Cited

U.S. PATENT DOCUMENTS

2016/0331528 A1* 11/2016 Parker ................... A61F 2/2412

OTHER PUBLICATIONS

[No authors listed] "Cardiovascular health crisis," *Lancet*, 376(9756):1874, Dec. 4, 2010.
Akamatsu et al., "Direct isolation of myofibroblasts and fibroblasts from bleomycin-injured lungs reveals their functional similarities and differences," *Fibrogenesis Tissue Repair*, 6(1):15, 2013.
Balguid et al., "Stress related collagen ultrastructure in human aortic valves—implications for tissue engineering," *J Biomech.*, 41(12):2612-2617, Epub Aug. 12, 2008.

(Continued)

*Primary Examiner* — Matthew Schall
(74) *Attorney, Agent, or Firm* — Fish & Richardson P.C.

(57) ABSTRACT

Systems and methods for producing biologic tissues are described. For example, this document provides electrospinning systems and culturing techniques to make biologic heart valve leaflets and fibrosa layers of native valve leaflet having nanofibrous substrate layer(s). In some implementations, a tri-layered leaflet with circumferentially, randomly, and radially oriented nanofibers that mimics morphologies of native leaflets.

17 Claims, 5 Drawing Sheets

(56) References Cited

OTHER PUBLICATIONS

Benton et al., "Photocrosslinking of gelatin macromers to synthesize porous hydrogels that promote valvular interstitial cell function," *Tissue Eng Part A.*, 15(11):3221-3230, Nov. 2009.

Bertazzo et al., "Nano-analytical electron microscopy reveals fundamental insights into human cardiovascular tissue calcification," *Nat Mater.*, 12(6):576-583, Epub Apr. 21, 2013.

Bertipaglia et al., "Cell characterization of porcine aortic valve and decellularized leaflets repopulated with aortic valve interstitial cells: the VESALIO Project (Vitalitate Exornatum Succedaneum Aorticum Labore Ingenioso Obtenibitur)," *Ann Thorac Surg.*, 75(4):1274-1282, Apr. 2003.

Bhardwaj et al., "Electrospinning: a fascinating fiber fabrication technique," *Biotechnol Adv.*, 28(3):325-347, Epub Jan. 25, 2010.

Biggs et al., "The use of nanoscale topography to modulate the dynamics of adhesion formation in primary osteoblasts and ERK/MAPK signalling in STRO-1+ enriched skeletal stem cells," *Biomaterials*, 30(28):5094-5103, Epub Jun. 21, 2009.

Chen et al., "A Novel Trilayered Polymer Scaffold Mimicking Native Aortic Valve Leaflet," ASME 2010 Summer Bioengineering Conference, Parts A and B, Naples, FL, Jun. 16-19, 2010.

Combs et al., "Heart valve development: regulatory networks in development and disease," *Circ Res.*, 105(5):408-421, Aug. 28, 2009.

Cuerrier et al., "Chronic over-expression of heat shock protein 27 attenuates atherogenesis and enhances plaque remodeling: a combined histological and mechanical assessment of aortic lesions," *PLoS One*, 8(2):e55867, Epub Feb. 7, 2013.

Cukierman et al., "Cell interactions with three-dimensional matrices," *Curr Opin Cell Biol.*, 14(5):633-639, Oct. 2002.

Della Rocca et al., "Cell composition of the human pulmonary valve: a comparative study with the aortic valve—the VESALIO Project. Vitalitate Exornatum Succedaneum Aorticum labore Ingegnoso Obtinebitur," *Ann Thorac Surg.*, 70(5):1594-1600, Nov. 2000.

Engelmayr et al., "Accordion-like honeycombs for tissue engineering of cardiac anisotropy," *Nat Mater.*, 7(12):1003-1010, Epub Nov. 2, 2008.

Engelmayr et al., "Prediction of extracellular matrix stiffness in engineered heart valve tissues based on nonwoven scaffolds," *Biomech Model Mechanobiol.*, 7(4):309-321, Epub Aug. 23, 2007.

Freeman et al., "Spectrum of calcific aortic valve disease: pathogenesis, disease progression, and treatment strategies," *Circulation*, 111(24):3316-3326, Jun. 21, 2005.

Furukawa, "Recent advances in research on human aortic valve calcification," *J Pharmacol Sci.*, 124(2):129-137, Epub Jan. 25, 2014.

Fuster and Kelly, editors, "Promoting Cardiovascular Health in the Developing World: A Critical Challenge to Achieve Global Health," National Academies Press, Jul. 29, 2010, 483 pages.

Goffin et al., "Focal adhesion size controls tension-dependent recruitment of alpha-smooth muscle actin to stress fibers," *J Cell Biol.* 172(2):259-268, Epub Jan 9, 2006.

Gould et al., "Cyclic strain anisotropy regulates valvular interstitial cell phenotype and tissue remodeling in three-dimensional culture," *Acta Biomater.*, 8(5): 1710-1719, May 2012.

Hinderer et al., "Engineering of a bio-functionalized hybrid off-the-shelf heart valve," *Biomaterials*, 35(7):2130-2139, Epub Dec. 13, 2013, print Feb. 2014.

Hinz, "Formation and function of the myofibroblast during tissue repair," *J Invest Dermatol.*, 127(3):526-537, Mar. 2007.

Jana et al., "Cells for tissue engineering of cardiac valves," *J Tissue Eng Regen Med.*, doi: 10.1002/term.2010. [Epub ahead of print] Feb. 25, 2015.

Jana et al., "Chitosan scaffolds with unidirectional microtubular pores for large skeletal myotube generation" *Adv Healthc Mater.*, 2(4):557-561, Epub Nov. 22, 2012, print Apr. 2013.

Jana et al., "Drug delivery in aortic valve tissue engineering," *J Control Release*, 196:307-323, Epub Oct. 22, 2014.

Jana et al., "Effect of nano- and micro-scale topological features on alignment of muscle cells and commitment of myogenic differentiation" *Biofabrication*, 6(3):035012, Epub May 30, 2014.

Jana et al., "In Vitro Model of a Fibrosa Layer of a Heart Valve," *ACS Appl Mater Interfaces.*, 7(36):20012-20020, Epub Sep. 1, 2015.

Jana et al., "Uniaxially aligned nanofibrous cylinders by electrospinning," *ACS Appl Mater Interfaces*, 4(9):4817-4824, Sep. 26, 2012.

Jana, "Fabrication of 3D aligned nanofibrous tubes by direct electrospinning," *J Mater Chem B*, 1(20):2575-2581, 2013.

Jana, "High-strength pristine porous chitosan scaffolds for tissue engineering," *Journal of Materials Chemistry*, 22(13):6291-6299, 2012.

Jana, "Scaffolds for tissue engineering of cardiac valves," *Acta Biomater.*, 10(7):2877-2893, Jul. 2014.

Leopold, "Cellular mechanisms of aortic valve calcification," *Circ Cardiovasc Interv*, 5(4):605-614, Aug. 1, 2012.

Leroux-Berger et al., "Pathologic calcification of adult vascular smooth muscle cells differs on their crest or mesodermal embryonic origin" J Bone Miner Res., 26(7):1543-1553, Jul. 2011.

Masoumi et al., "Electro spun PGS:PCL microfibers align human valvular interstitial cells and provide tunable scaffold anisotropy," *Adv Healthc Mater.*, 3(6):929-939, Epub Jan. 22, 2014.

Masoumi et al., "Tri-layered elastomeric scaffolds for engineering heart valve leaflets," *Biomaterials*, 35(27):7774-7785, Sep. 2014.

Masoumi et al., "Valvular interstitial cell seeded poly(glycerol sebacate) scaffolds: toward a biomimetic in vitro model for heart valve tissue engineering," *Acta Biomater.*, 9(4):5974-5988, Epub Jan. 5, 2013.

Mavrilas et al., "An approach to the optimization of preparation of bioprosthetic heart valves," *J Biomech.*, 24(5):331-339, 1991.

Nerurkar et al., "Nanofibrous biologic laminates replicate the form and function of the annulus fibrosus," *Nat Mater.*, 8(12):986-992, Dec. 2009.

Nishimura, "Cardiology patient page: Aortic valve disease," *Circulation*, 106(7):770-772, Aug. 13, 2002.

Patel et al., "Highly elastomeric poly(glycerol sebacate)-co-poly(ethylene glycol) amphiphilic block copolymers," *Biomaterials*, 34(16):3970-3983, May 2013.

Rabkin-Aikawa et al., "Dynamic and reversible changes of interstitial cell phenotype during remodeling of cardiac valves," *J Heart Valve Dis.*, 13(5):841-847, Sep. 2004.

Rajamannan et al., "Calcific aortic valve disease: not simply a degenerative process: A review and agenda for research from the National Heart and Lung and Blood Institute Aortic Stenosis Working Group. Executive summary: Calcific aortic valve disease—2011 update," *Circulation*, 124(16):1783-1791, Oct. 18, 2011.

Ricupero et al., "Apigenin decreases expression of the myofibroblast phenotype," *FEBS Lett.*, 506(1):15-21, Sep. 28, 2001.

Rouabah et al., "Thermophysical and Mechanical Properties of Polystyrene: Influence of Free Quenching," ISRN Polymer Science, 2012:8, Article 161364, 2012.

Rutledge et al., "Formation of fibers by electrospinning," *Adv Drug Deliv Rev.*, 59(14):1384-1391, Dec. 10, 2007.

Sacks et al., "Heart valve function: a biomechanical perspective," Philos Trans R Soc Lond B Biol Sci., 362(1484):1369-1391, Aug. 29, 2007.

Sant et al., "Effect of biodegradation and de novo matrix synthesis on the mechanical properties of valvular interstitial cell-seeded polyglycerol sebacate-polycaprolactone scaffolds," *Acta Biomater.*, 9(4):5963-5973, Epub Nov. 17, 2012.

Schoen, "Evolving concepts of cardiac valve dynamics: the continuum of development, functional structure, pathobiology, and tissue engineering," *Circulation*, 118(18):1864-1880, Oct. 28, 2008.

Sheets et al., "Cell-Fiber Interactions on Aligned and Suspended Nanofiber Scaffolds," *J Biomater Tissue Eng.*, 3(4):355-368, Aug. 1, 2013.

Simionescu et al., "Form follows function: advances in trilayered structure replication for aortic heart valve tissue engineering," *J Healthc Eng.*, 3(2):179-202, Jun. 1, 2012.

Staico et al., "Coronary embolism and calcified aortic valve: is there a correlation?" J Thromb Thrombolysis, 34(3):425-427, Oct. 2012.

Starborg et al., "Electron microscopy in cell-matrix research," Methods (San Diego, Calif)., 45:53-64, 2008.

(56) References Cited

OTHER PUBLICATIONS

Stella et al., "On the biaxial mechanical properties of the layers of the aortic valve leaflet," *J Biomech Eng.*, 129(5):757-766, Oct. 2007.

Tan et al., "The effects of sterilization and storage treatments on the stress-strain behavior of aortic valve leaflets," *Ann Thorac Surg.*, 22(2):188-194, Aug. 1976.

Tedder et al., "Assembly and testing of stem cell-seeded layered collagen constructs for heart valve tissue engineering," *Tissue Eng Part A.*, 17(1-2):25-36, Jan. 2011.

Thayer et al., "The effects of combined cyclic stretch and pressure on the aortic valve interstitial cell phenotype," *Ann Biomed Eng.*, 39(6):1654-1667, Jun. 2011.

Tseng et al., "Fabrication and mechanical evaluation of anatomically-inspired quasilaminate hydrogel structures with layer-specific formulations," Ann Biomed Eng., 41(2):398-407, Feb. 2013.

Wang et al., "A tough biodegradable elastomer," *Nat Biotechnol.*, 20(6):602-606, Jun. 2002.

Wang et al., "Hydrogels preserve native phenotypes of valvular fibroblasts through an elasticity-regulated PI3K/AKT pathway," Proc Natl Acad Sci U S A., 110(48):19336-19341, Nov. 26, 2013.

Yacoub et al., "Novel approaches to cardiac valve repair: from structure to function: Part I," *Circulation*, 109(8):942-950, Mar. 2, 2004.

Zhan et al., "Multifunctional aliphatic polyester nanofibers for tissue engineering," *Biomatter*, 2(4):202-212, Oct.-Dec. 2012.

\* cited by examiner

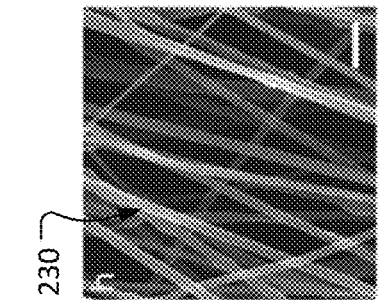
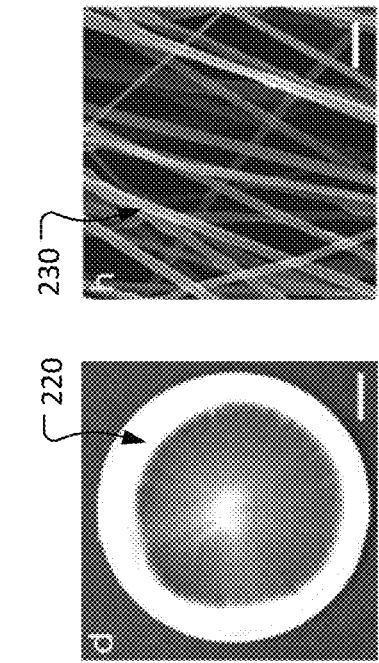
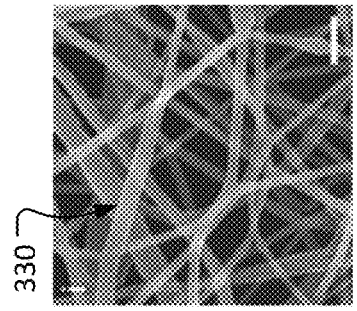
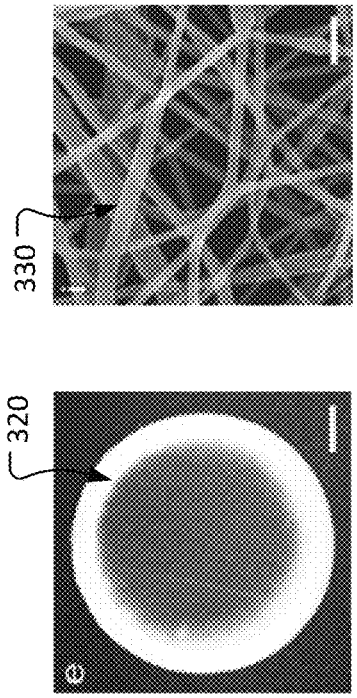
FIG. 3
FIG. 4
FIG. 5
FIG. 6
FIG. 7
FIG. 8
FIG. 9
FIG. 10

NANOFIBROUS BIOLOGIC HEART VALVE LEAFLETS AND FIBROSA LAYER OF A LEAFLET

CROSS-REFERENCE TO RELATED APPLICATIONS

This application claims the benefit of U.S. Provisional Application Ser. No. 62/154,880, filed Apr. 30, 2015. The disclosure of the prior application is considered part of (and is incorporated by reference in) the disclosure of this application.

BACKGROUND

1. Technical Field

This document relates to systems and methods for producing biologic tissue. For example, this document relates to using electrospinning systems and culturing techniques to make biologic heart valve leaflets having multiple nanofibrous substrate layers.

2. Background Information

Cardiac valves control blood flow within the heart by opening and closing their leaflets to create and release pressure differentials. Leaflets are primarily composed of valvular interstitial cells (VICs) residing in three apposed layers—a circumferentially oriented fibrosa layer, a randomly oriented spongiosa layer, and a radially oriented ventricularis layer. Collagen, collagen/proteoglycan, and collagen/elastin are the predominant extracellular matrix components in these layers, respectively. A diseased or damaged leaflet may result in valvular regurgitation and/or stenosis that detrimentally affects blood flow through the heart. In some cases, such leaflet dysfunctionalities are triggered by adverse biochemical factors and mechanical stresses on the VICs.

In a healthy heart valve leaflet, VICs show quiescent fibroblast phenotype; however, their pathogenic myofibroblast phenotype is observed in its diseased counterpart. During fetal leaflet development, and in remodeling of fully-grown leaflets, VICs show active myofibroblast phenotype. Further, they show fibroblast phenotype on a soft substrate and active myofibroblast phenotypes on a substrate with high mechanical properties. Active myofibroblasts may cause contractility and in the presence of adverse environment, they may be transformed to pathogenic, which is not desirable.

SUMMARY

This document provides systems and methods for producing biologic tissue. For example, this document provides electrospinning systems and culturing techniques to make biologic heart valve leaflets having multiple nanofibrous substrate layers.

In one implementation, a biologic heart valve leaflet includes a synthetic trilayered nanofibrous substrate material. The synthetic trilayered nanofibrous substrate material includes a first layer comprising a radially oriented nanofibrous substrate; a second layer comprising a randomly oriented nanofibrous substrate; and a third layer comprising a circumferentially oriented nanofibrous substrate. The second layer is disposed on a surface of the first layer, and the third layer is disposed on a surface of the second layer.

Such a biologic heart valve leaflet may optionally include one or more of the following features. The first layer, the second layer, and the third layer may each be made using an electrospinning process. The second layer may be disposed on the surface of the first layer by electrospinning the second layer onto the surface of the first layer. The third layer may be disposed on the surface of the second layer by electrospinning the third layer onto the surface of the second layer. The first layer, the second layer, and the third layer may comprise nanofibers having diameters of about 340+/−87 nm. The nanofibers may comprise one or more from the group consisting of polycaprolactone, polyglycerol sebacate, polyglycolic acid, collagen, and poly(lactide-co-glycolide). The biologic heart valve leaflet may further comprise valvular interstitial cells. The valvular interstitial cells may comprise human valvular interstitial cells. The biologic heart valve leaflet may further comprise one or more polypeptides produced by the valvular interstitial cells. The one or more polypeptides may comprise one or more of types of collagen, collagen/proteoglycan, and elastin.

In another implementation, a method of making a synthetic trilayered nanofibrous substrate material for biologic heart valve leaflets includes electrospinning a first layer comprising a radially oriented nanofibrous substrate; electrospinning a second layer comprising a randomly oriented nanofibrous substrate; and electrospinning a third layer comprising a circumferentially oriented nanofibrous substrate. The second layer is disposed on a surface of the first layer, and the third layer is disposed on a surface of the second layer.

Such a method of making a synthetic trilayered nanofibrous substrate material for biologic heart valve leaflets may optionally include one or more of the following features. The second layer may be disposed on the surface of the first layer by electrospinning the second layer onto the surface of the first layer. The third layer may be disposed on the surface of the second layer by electrospinning the third layer onto the surface of the second layer. The method may further comprise culturing the trilayered nanofibrous substrate material with valvular interstitial cells. The valvular interstitial cells may be porcine or human valvular interstitial cells. The culturing may be in the presence of ascorbic acid. The method may include culturing the trilayered nanofibrous substrate material with about 1×106 to about 3×106 valvular interstitial cells. The method may include culturing the trilayered nanofibrous substrate material with the valvular interstitial cells for a time-period of 3 weeks to 6 weeks.

In another implementation, a synthetic material that mimics a fibrosa layer of a native heart valve leaflet includes a substrate of electrospun circumferentially oriented nanofibers.

Such a synthetic material that mimics a fibrosa layer of a native heart valve leaflet may optionally include one or more of the following features. The nanofibers may have diameters of about 340+/−87 nm. The nanofiber's diameters can vary from 100 nm to 2-3 µm depending on the materials for electrospinning and electrospinning parameters. The nanofibers may comprise one from the group consisting of polycaprolactone, polyglycerol sebacate, polyglycolic acid, collagen, and poly(lactide-co-glycolide). In addition, other electro-spinnable biomaterials can be used to develop the nanofibers. The material may further comprise valvular interstitial cells. The valvular interstitial cells may be porcine or human valvular interstitial cells. The material may further comprise one or more polypeptides produced by the valvular interstitial cells. The one or more polypeptides may comprise one or more types of collagen, proteoglycan, and elastin.

In another implementation, a method of making a synthetic material that mimics a fibrosa layer of a native heart valve leaflet includes electrospinning a circumferentially oriented layer of nanofibers.

Such a method of making a synthetic material that mimics a fibrosa layer of a native heart valve leaflet may optionally include one or more of the following features. The method may further comprise culturing the material with valvular interstitial cells. The valvular interstitial cells may be porcine or human valvular interstitial cells. The culturing may be in the presence of ascorbic acid. The culturing the material may be performed with about $1 \times 10^6$ to about $3 \times 10^6$ valvular interstitial cells. The culturing the material with the valvular interstitial cells may occur for a time-period of 3 weeks to 6 weeks.

Particular embodiments of the subject matter described in this document can be implemented to realize one or more of the following advantages. Applying an electrospinning process as provided herein, a trilayered nanofibrous prosthetic substrate comprising circumferentially, randomly, and radially oriented layers that exist in a native valve leaflet can be constructed. The trilayered nanofibrous prosthetic substrate exhibits elastomeric properties suitable for biologic leaflet generation. VICs cultured statically in the trilayered substrate in presence of ascorbic acid produce sufficient collagen (the main component of a heart valve native leaflet). After such culturing, the tensile curve profile of the developed trilayered leaflet construct is advantageously similar to that of native leaflets. Orientations and structure of cultured VICs and deposited collagen, collagen/proteoglycans, and collagen/elastin in the equivalent fibrosa, spongiosa and ventricularis layers of the biologic trilayered leaflet constructs are comparable to those in native leaflets. Using the heart valve leaflet constructs provided herein, a biomimicked heart valve can be created by modifying the design of the substrate. Moreover, biomimicked leaflet constructs may provide a substitute to limited in vivo resources for studying various heart valve diseases.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 3 is plan view of an example ring-with-dot collector that can be used with an electrospinning process to prepare a layer of radially oriented nanofibers in accordance with some embodiments provided herein.

FIG. 4 is a side view of the ring-with-dot collector of FIG. 3 that is positionally fixed and electrically grounded by a clamp in preparation for the electrospinning process.

FIG. 5 is a photo of a radially oriented nanofibrous layer produced by the electrospinning process using the ring-with-dot collector of FIG. 3.

FIG. 6 is an SEM image of the radially oriented nanofibers of FIG. 5.

FIG. 7 is plan view of an example ring collector that can be used with an electrospinning process to prepare a layer of randomly oriented nanofibers in accordance with some embodiments provided herein.

FIG. 8 is a side view of the ring collector of FIG. 7 that is positionally fixed and electrically grounded by a clamp in preparation for the electrospinning process.

FIG. 9 is a photo of a randomly oriented nanofibrous layer produced by the electrospinning process using the ring collector of FIG. 7.

FIG. 10 is an SEM image of the randomly oriented nanofibers of FIG. 9.

Like reference numbers represent corresponding parts throughout.

DETAILED DESCRIPTION

This document provides systems and methods for producing biologic tissue. For example, this document provides electrospinning systems and culturing techniques to make biologic heart valve leaflets having multiple nanofibrous substrate layers.

In some embodiments provided herein, engineered tissue substrates (also referred to herein as "scaffolds") are designed to meet at least one or more of the following objectives: 1) the scaffolds have low stiffnesses, close to that of a native leaflet so that VICs are less likely to attain contractile myofibroblast phenotype, 2) the scaffolds are made of nanofibers that mimic the nanofibril-morphology of collagen, elastin and other proteins so that cultured VICs can grow in a compatible microenvironment, and 3) the scaffolds have a trilayered structure mimicking the layered orientation of a native leaflet.

Trilayered nanofibrous (TN) substrates that mimic the morphologies of the fibrosa, spongiosa, and ventricularis layers of a native leaflet are provided herein. The substrates exhibit elastomeric properties substantially as seen in native valve leaflets. The biologic trilayered leaflet constructs (TC) are quite equivalent to fibrosa, spongiosa, and ventricularis layers in the native leaflets with a presence of collagen, collagen/proteoglycans, and collagen/elastin, respectively, are present in some embodiments provided herein. The stress-strain profiles of the (TC) provided herein and those of native leaflets are advantageously similar. The vimentin, α-SMA, and Col1A1 gene expressions of VICs in some scaffolds provided herein indicate that the trilayered nanofibrous microenvironment is responsible for the transformation of TN substrate into a growing TC in vitro.

Figure 1:
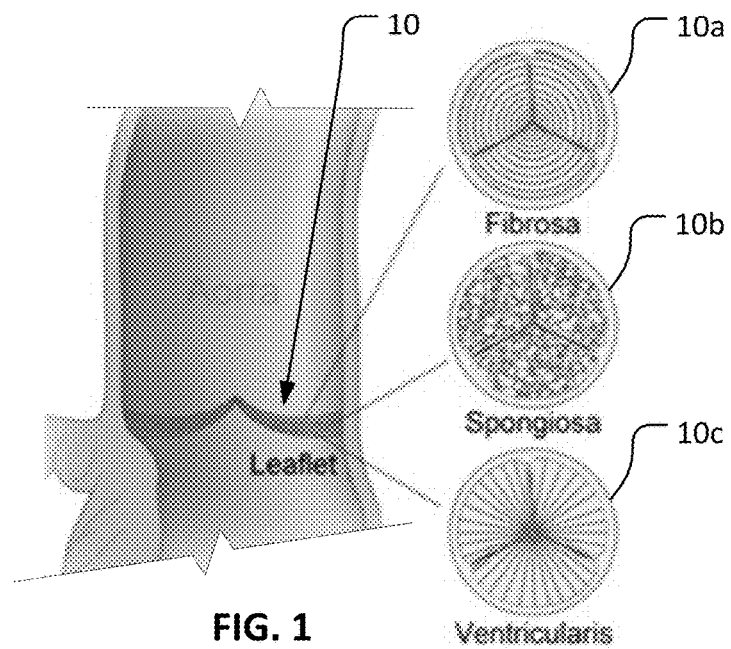
FIG. 1 is a schematic diagram of a native heart valve leaflet that is comprised of a circumferentially oriented fibrosa layer, a randomly oriented spongiosa layer, and a radially oriented ventricularis layer.

With reference to FIG. 1, an example aortic valve native leaflet 10 is comprised of a trilayered structure. That is, native leaflet 10 includes a circumferentially oriented fibrosa layer 10a, a randomly oriented spongiosa layer 10b, and a radially oriented ventricularis layer 10c. Spongiosa layer 10b is generally disposed between fibrosa layer 10a and ventricularis layer 10c. Collagen, collagen/proteoglycan, and collagen/elastin respectively, are the predominant extracellular matrix components in these layers 10a, 10b, and 10c. As appreciated by one of skill in the art, leaflets, the prime component of a heart valve, have diverse structural, mechanical, and bimolecular properties. Thus, in the context of heart valve tissue engineering, biomimicking of heart valve leaflets has remained challenging.

Figure 2:
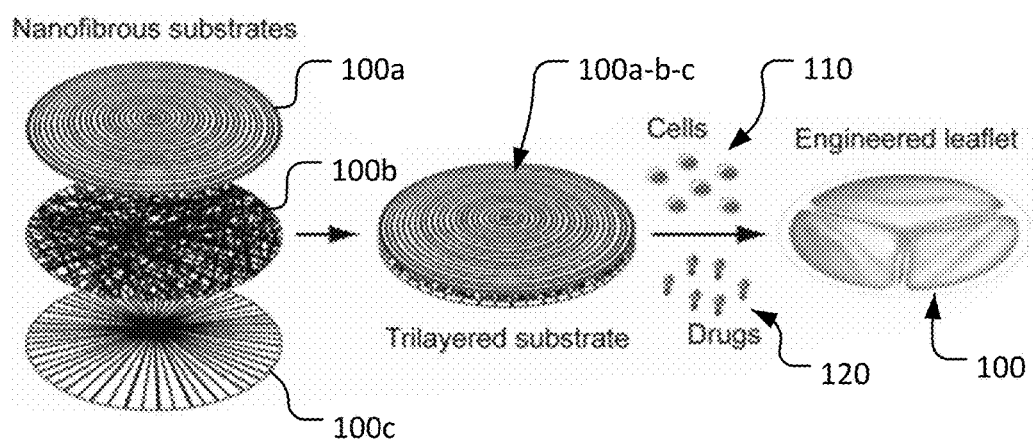
FIG. 2 is a schematic diagram of a trilayered nanofibrous prosthetic leaflet substrate constructed of a circumferentially oriented nanofibrous (CON) layer, a randomly oriented nanofibrous (RON) layer, and a radially oriented nanofibrous layer, in accordance with some embodiments provided herein.

With reference to FIG. 2, a process for making an engineered leaflet 100 having multiple nanofibrous substrate layers is provided herein. As described further herein, engineered leaflet 100 is comprised of a layer of circumferentially oriented nanofibers 100a, a layer of randomly oriented nanofibers 100b, and a layer of radially oriented nanofibers 100c. Such layers of nanofibers 100a, 100b, and 100c are combined to form a unitary trilayered substrate 100a-b-c. In some embodiments, VICs (valvular interstitial cells) 110 are cultured statically in the trilayered substrate 100a-b-c in presence of ascorbic acid to thereby produce sufficient collagen (the main component of a native leaflet). Such VICs can be human VICs, for example. Additionally, in some embodiments one or more growth factors/drugs 120 are applied in trilayered substrate 100a-b-c to result in functional engineered leaflet 100. Engineered leaflet 100 mimics the morphologies of the fibrosa, spongiosa, and ventricularis layers of a native leaflet.

FIGS. 3-14 illustrate how the layers of a trilayered substrate (e.g., trilayered substrate 100a-b-c) can be fabricated using an electrospinning process. Electrospinning is a versatile technique that can be used to prepare nanofibrous substrates. Electrospinning is applicable to most polymers, is easy handling, and cost-effective. In the electrospinning process, the shape and form of the collectors influence orientations of the depositing fibers. Applying these principles, electrospinning can be used to sequentially create three differing nanofibrous layers one over another to produce a trilayered nanofibrous (TN) substrate that mimics the morphological structure of a native aortic valve leaflet.

With reference to FIG. 3, an example ring-with-dot collector 200 can be used in conjunction with an electrospinning process (as described further elsewhere herein) to prepare a layer of radially oriented nanofibers (e.g., layer of radially oriented nanofibers 100c described in reference to FIG. 2). In some embodiments, ring-with-dot collector 200 is comprised of aluminum materials, or one or more other electrically conductive materials. In some implementations, a polycaprolactone (PCL) ring-layer, about 0.25 mm thick, was deposited on ring-with-dot collector 200 by pouring an about 18% (wt/v) PCL solution on it. The resulting PCL ring later acts as a frame to hold the spun nanofibers intact after removing them together from ring-with-dot collector 200. In some implementations, an about 9% (wt/v) PCL solution can be electrospun on ring-with-dot collector 200 to produce generally radially oriented nanofibers. Between the dot and the ring, a magnetic field is formed while electrospinning that pulls one end of a depositing nanofiber towards dot and another end towards ring radially. Thus, deposited fibers are generally radially oriented.

With reference to FIG. 4, ring-with-dot collector 200 can be positionally fixed and electrically grounded using a mounting assembly 210. Mounting assembly 210 can be used to maintain the position of ring-with-dot collector 200 and to present ring-with-dot collector 200 to a spinneret of an electrospinning system (not shown) during operation of an electrospinning process.

With reference to FIGS. 5 and 6, using ring-with-dot collector 200 in conjunction with the electrospinning process, a layer of radially oriented nanofibers 220 can be fabricated. As shown in FIG. 6, adjacent nanofibers 230 are predominantly oriented in a common direction.

With reference to FIG. 7, an example ring collector 300 can be used in conjunction with an electrospinning process (as described further elsewhere herein) to prepare a layer of randomly oriented nanofibers (e.g., layer of randomly oriented nanofibers 100b described in reference to FIG. 2). In some embodiments, ring collector 300 is comprised of aluminum materials, or one or more other electrically conductive materials. In some implementations, layer of radially oriented nanofibers 220 (refer to FIG. 5) is placed onto ring collector 300 prior to electrospinning the randomly oriented fibers. Therefore, the randomly oriented nanofibers can be deposited onto the radially oriented nanofibers to create a bilayer construct. By using a ring rather than a plate, the resulting randomly oriented nanofibrous layer is quite porous.

With reference to FIG. 8, ring collector 300 can be positionally fixed and electrically grounded using a mounting assembly 310. Mounting assembly 310 can be used to maintain the position of ring collector 300 and to present ring collector 300 to a spinneret of an electrospinning system (not shown) during operation of an electrospinning process.

With reference to FIGS. 9 and 10, using ring collector 300 in conjunction with the electrospinning process, a layer of randomly oriented nanofibers 320 can be fabricated. As shown in FIG. 10, nanofibers 330 are generally oriented in a random fashion directionally.

Figure 11:
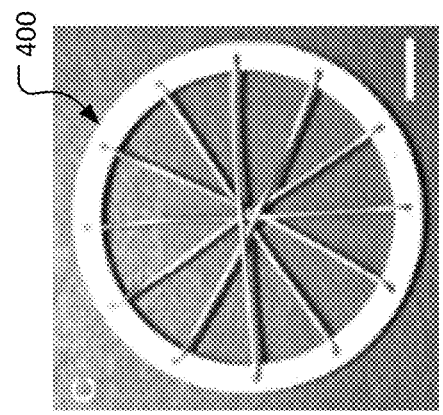
FIG. 11 is plan view of an example spokes-in-ring collector that can be used with an electrospinning process to prepare a layer of circumferentially oriented nanofibers in accordance with some embodiments provided herein.

With reference to FIG. 11, an example spokes-in-ring collector 400 can be used in conjunction with an electrospinning process (as described further elsewhere herein) to prepare a layer of circumferentially oriented nanofibers (e.g., layer of circumferentially oriented nanofibers 100a described in reference to FIG. 2). In some embodiments, spokes-in-ring collector 400 is comprised of aluminum materials, or one or more other electrically conductive materials. In some implementations, the bilayer construct of: (i) radially oriented nanofibers 220 (refer to FIG. 5) and (ii) randomly oriented nanofibers 320 (refer to FIG. 9) is placed onto ring collector 400 prior to electrospinning the circumferentially oriented fibers. Therefore, the circumferentially oriented nanofibers can be deposited onto the bilayer construct of nanofibers to create a trilayer construct of nanofibers.

Figure 12:
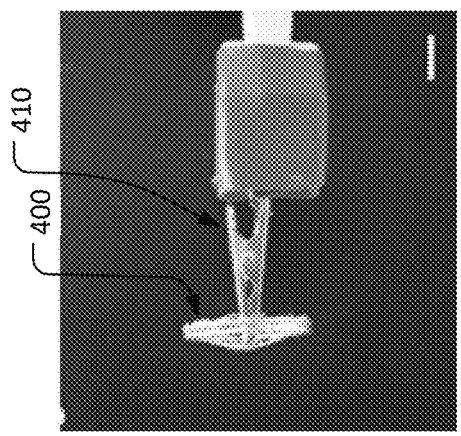
FIG. 12 is a side view of the spokes-in-ring collector of FIG. 11 that is positionally fixed and electrically grounded by a clamp in preparation for the electrospinning process.

With reference to FIG. 12, spokes-in-ring collector 400 can be positionally fixed and electrically grounded using a mounting assembly 410. Mounting assembly 410 can be used to maintain the position of spokes-in-ring collector 400 and to present spokes-in-ring collector 400 to a spinneret of an electrospinning system (not shown) during operation of an electrospinning process.

Figure 13:
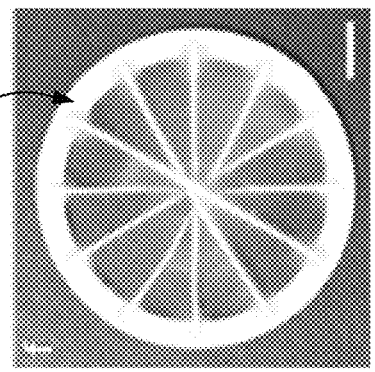
FIG. 13 is a photo of a circumferentially oriented nanofibrous layer produced by the electrospinning process using the spokes-in-ring collector of FIG. 11.
Figure 14:
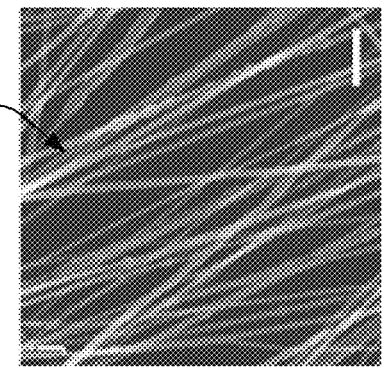
FIG. 14 is an SEM image of the circumferentially oriented nanofibers of FIG. 13.

With reference to FIGS. 13 and 14, using spokes-in-ring collector 400 in conjunction with the electrospinning process, a layer of circumferentially oriented nanofibers 420 can be fabricated. As shown in FIG. 14, adjacent nanofibers 430 are predominantly oriented in a common direction.

Figures 15, 16:
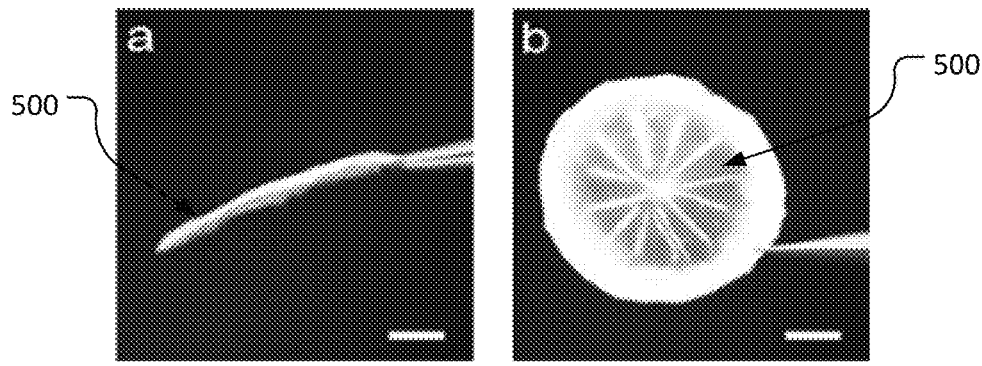
FIG. 15 is a photo showing a plan view of a trilayered nanofibrous substrate in accordance with some embodiments provided herein. It also illustrates the standalone characteristics of the trilayered nanofibrous substrate.
FIG. 16 is a photo showing a side view of the trilayered nanofibrous substrate of FIG. 15.

With reference to FIGS. 15 and 16, a trilayered nanofibrous (TN) substrate 500 as constructed, for example, as described above can provide a prosthetic material that is structurally strong. FIG. 15 illustrates the shape maintaining characteristics of TN substrate 500 when held in a vertical orientation. FIG. 16 illustrates the shape maintaining characteristics of TN substrate 500 when held in a horizontal orientation.

Figures 17, 18, 19:
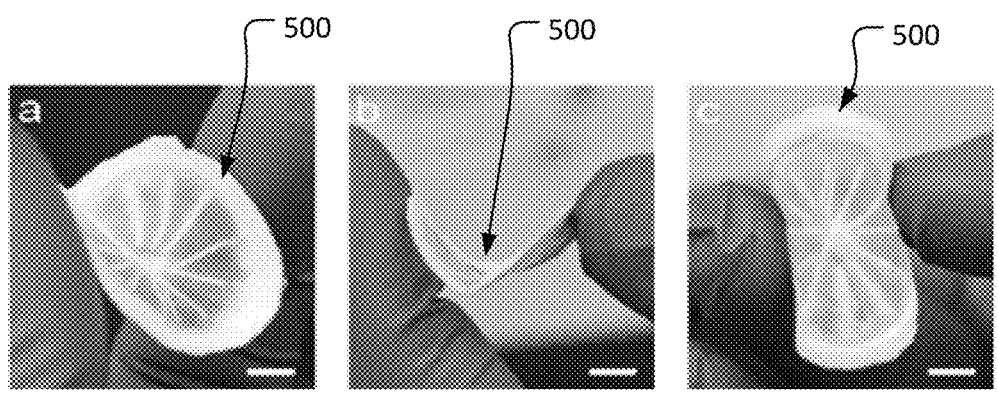
FIGS. 17-19 are photos illustrating the suppleness of the trilayered nanofibrous substrate of FIG. 15.

With reference to FIGS. 17-19, TN substrate 500 as constructed, for example, as described above can provide a prosthetic material that is supple and resilient. Accordingly, TN substrate 500 can be bent, advantageously, into various configurations without causing structural failure or permanent deformation of TN substrate 500.

Figure 20:
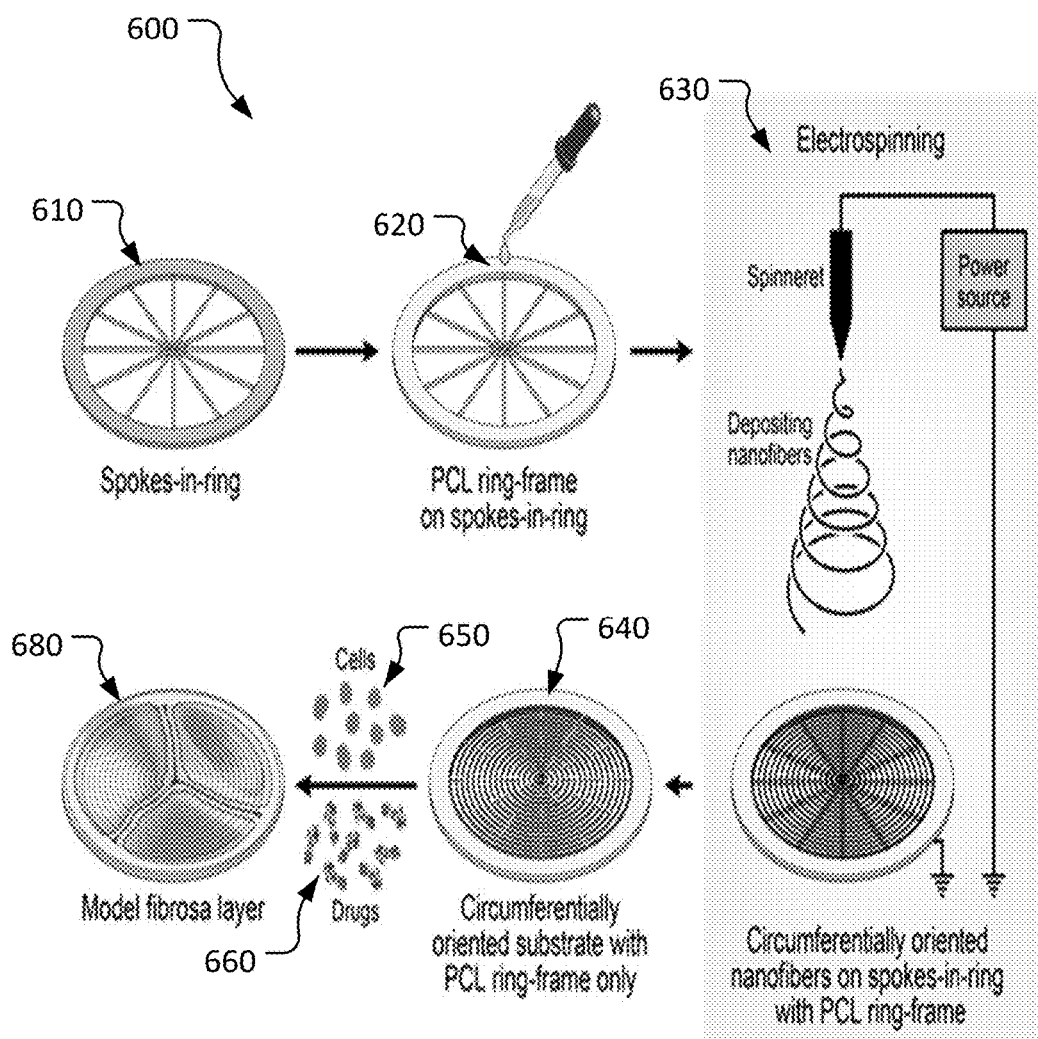
FIG. 20 is a schematic diagram of an example process for producing a biologic circumferentially oriented fibrosa layer in accordance with some embodiments provided herein.

With reference to FIG. 20, an example multi-step process 600 can be used to create a model fibrosa layer 680. The fibrosa layer of a native cardiac aortic valve is composed mostly of a dense network of type I collagen fibers oriented in circumferential direction. This is the main layer which bears the tensile load and responds to the high stress on a native leaflet. In heart valve tissue engineering, generating of this layer is challenging. Process 600 is aimed at developing an artificial fibrosa layer 680 that closely mimicks the properties of the fibrosa layer of a native aortic leaflet.

Process 600 includes providing a spokes-in-ring collector 610 and depositing a polycaprolactone (PCL) ring layer 620, about 0.25 mm thick, on spokes-in-ring collector 610 by pouring an about 18% (wt/v) PCL solution on it. The resulting PCL ring layer 620 later acts as a frame to hold the spun nanofibers intact after removing them together from spokes-in-ring collector 610.

Process 600 further includes electrospinning 630 to deposit nanofibers in a circumferentially oriented fashion on spokes-in-ring collector 610. In some implementations, a circumferentially oriented nanofibrous (CON) substrate is produced by electrospinning an about 9 wt % PCL solution on spokes-in-ring collector 610. Between the spokes, a magnetic field is formed that pulls one end of a nanofiber towards one spoke and another end towards the adjacent spoke perpendicularly, thus depositing fibers generally concentrically. PCL is selected for some implementations because it is easy to spin, has slow biodegradation property and can be applied for in vivo study. The resulting nanofibrous substrates have a spokes-in-ring shape with circumferentially oriented PCL nanofibers connected to adjacent nanofibrous spokes.

Nanofibrous substrate 640 with the PCL-layered ring-frame tends to separate easily from spokes-in-ring collector 610. Unlike some other generally used nanofibrous substrates in tissue engineering, these CON substrates 640 do not require structural support such as a glass coverslip at their back due to presence of PCL-layered ring-frame at their peripheries. That is, in some embodiments these nanofibrous substrates 640 are fully standalone. In some embodiments of process 600, VICs (valvular interstitial cells) 650 are cultured statically in nanofibrous substrate 640 in presence of ascorbic acid to thereby produce sufficient collagen (the main component of a native leaflet). Additionally, in some embodiments one or more growth factors/drugs 660 are used to treat nanofibrous substrate 640 to result in model fibrosa layer 680.

A unique morphologically biomimicked substrate 640 that is pliable but structurally strong, with circumferentially oriented nanofibers, can be fabricated using process 600 (by electrospinning on a novel-designed collector 610). The circumferentially oriented substrate 640 has low mechanical properties; thus, cultured VICs showing fibroblast phenotype that generally is observed in healthy aortic leaflets may be used in the preparation of artificial fibrosa layer 680. In fact, VICs also can be used in the preparation of engineered leaflet 100. VICs in engineered leaflet 100 and artificial fibrosa layer 680 can demonstrate gene and protein expression and morphology that mimic those in the a native leaflet and fibrosa layer of a native aortic leaflet, respectively.

VICs can be isolated from aortic valve leaflets obtained from, for example, one or more donor animal hearts (e.g., pig hearts). In some embodiments, for example, a donor leaflet can be washed in a saline solution (e.g., phosphate buffered saline) and digested in trypsin. The endothelial layer can be gently removed from the leaflet surfaces, and the leaflet can be digested in collagenase to isolate the VICs, which can be cultured and expanded.

To culture an engineered leaflet (or a layer thereof, such as artificial fibrosa layer 680) with VICs, the leaflet or layer can be sterilized (e.g., by incubating in ethanol) and then seeded with VICs (e.g., about $1 \times 10^6$ to about $3 \times 10^6$ VICs, or about $0.5 \times 10^6$ to about $2 \times 10^6$ VICs, or about $1 \times 10^6$ to about $2 \times 10^6$ VICs) in a media containing ascorbic acid to induce expression of proteins such as collagen, elastin, vimentin, and $\alpha$-SMA, for a suitable length of time (e.g., about 3 weeks to 6 weeks, or about 2 weeks to about 7 weeks, or about 4 weeks to about 5 weeks). Methods for assessing the number and/or proliferation of the VICs, as well as the level of protein expression by the VICs, include those that are known in the art and commercially available, and those that are described in the Examples herein. For example, to measure the level of collagen, cultures or leaflet samples can be digested with papain type III, and supernatants can be collected for collagen quantification. Elastin quantification can be performed using, for example, a Fastin kit (Biocolor, USA). Analysis of protein expression also can be achieved by measuring RNA levels for genes of interest, as known in the art and described herein, for example.

In some cases, the thickness of the trilayered nanofibrous substrate can vary from about 60 μm to about 300 μm depending on fiber diameter (i.e., the materials to spin and electrospinning parameters) and time of spinning. The thickness of the trilayered nanofibrous substrate could be as per requirement. The thickness of the circumferentially, randomly and/or radially oriented nanofibrous substrate layers can be proportionate to the thickness of the native fibrosa, spongiosa and ventricularis layers, respectively. If necessary, the thickness of the circumferentially, randomly and radially oriented nanofibrous substrate layers could be as per requirement.

In some cases, the mechanical properties of the trilayered nanofibrous substrate can be tuned as per requirement by varying the one material or combination of materials in nanofibers. For example, in some cases an addition of polyglycerol sebacate to polycaprolactone can produce appropriate mechanical and elastomeric properties of trilayered nanofibrous substrate.

With more time of culturing, the amount of collagen, proteoglycan and elastin will be deposited, and their amounts can be similar to the corresponding amounts in native leaflet.

Example #1

Through electrospinning, a trilayered nanofibrous substrate that mimics the morphologies of three layers of a native heart valve leaflet was developed. The elastomeric property of the substrate was favorable for leaflet development. Orientations and morphologies of cultured VICs and deposited collagen, collagen/proteoglycans and collagen/elastin in equivalent fibrosa, spongiosa and ventricularis layers of trilayered leaflet constructs were comparable to those in native leaflets. Similar tensile curve profiles were observed in both leaflet constructs and native leaflets. Comparable expressions of vimentin and Col1A1 gene and higher expression of α-SMA by VICs in leaflet constructs with respect to the native leaflets indicate that leaflet constructs were in developing stage. As we were successful in biomimicking a native leaflet in vitro through static culturing, it can be stated that morphological influence may substitute the dynamic environment present in vivo for Electrospinning is a versatile technique to prepare nanofibrous substrates due to its applicability to most polymers, easy handling and cost-effectiveness. In this technique, shape and form of the collectors influence orientations of the depositing fibers. Applying this principle, we electrospun three nanofibrous layers sequentially to develop a trilayered nanofibrous (TN) substrate that mimics the morphological structure of a native aortic valve leaflet (refer to FIGS. 1 and 2). First, we designed three aluminum collectors of same dimension to fabricate those three nanofibrous layers. A collector (ring-with-dot collector) intended to produce radially oriented nanofibers was a ring with a dot at its center (refer to FIG. 3). A simple ring collector (refer to FIG. 7) was used to produce randomly oriented nanofibers. A collector (spokes-in-ring collector) made of a ring with twelve spokes was used to produce circumferentially oriented fibers (refer to FIG. 11). A ~0.25 mm-thick polycaprolactone (PCL) ring-layer was made on the ring-with-dot collector by pouring 18% (wt/v) PCL solution on it. This PCL ring worked as a frame to hold the spun nanofibers intact after removing them together from the collector. 9% (wt/v) PCL solution was electrospun on that collector to produce radially oriented nanofibers (FIGS. 5 and 6). Between the dot and the ring, a magnetic field was formed that pulled one end of a depositing nanofiber towards dot and another end towards ring radially; thus, deposited fibers were radially oriented. PCL was used due to its slow degradation rate, ease of electrospinning and favorable to in vivo application. The PCL ring with radially oriented nanofibrous layer came out easily from the collector. This nanofibrous layer was then placed on the ring collector and electrospinning was performed. In general, a metal plate is used to produce randomly oriented nanofibrous substrate. However, we made a randomly oriented nanofibrous layer without any metal plate attached to the back of ring collector to make the layer highly porous (FIGS. 9 and 10). Thus, a randomly oriented layer was fabricated over the radially oriented layer i.e. a substrate containing two layers was created. We then placed this bilayer substrate on the spokes-in-ring collector. After electrospinning, we obtained a circumferentially oriented nanofibrous layer (FIGS. 13 and 14) on the bilayer substrate i.e. a nanofibrous trilayered substrate with three nanofiber-orientations (radial, random and circumferential, sequentially) was created. Between the spokes, a magnetic field was formed that pulled two ends of depositing nanofibers towards two consecutive spokes perpendicularly and thus deposited fibers were concentric. Deposited nanofibers on the metal spokes created nanofibrous which kept the circumferentially oriented fibers intact after removal of the collector. The structure of a trilayered substrate with its nanofiber orientations could be observed. Although, layer-by-layer electrospinning was performed to produce this trilayered substrate, the layers could not be separated without damaging the nanofibers and their morphologies. Fiber diameter of nanofibers in the substrates was 340±87 nm. Unlike other nanofibrous membrane-based substrates used in tissue engineering, these trilayered substrates are fully standalone due to presence of the PCL ring-frames at their peripheries. Thus, there will be no underlying platform (generally coverslip) that can influence the culturing VICs in the TN substrate. Furthermore, like a native leaflet, these substrates are flexible (FIGS. 17-19). They also returned to their original form if deformed.

Uniaxial tensile testing on native leaflet and TN substrate samples was performed along the circumferential direction to determine their mechanical properties. A third of a TN substrate was almost equivalent to a native leaflet in terms of shape and oriented layers. Stress-strain profile of native leaflets showed a non-linear trend with more than 120% elongation confirming its elastomeric properties. At the onset of tensile test, the straightening of leaflet occurred due to its non-linear shape and presence of undulatedly arranged collagen fibrils, and afterwards, the leaflet was elongated with increase of tensile load. The moduli at these two regions were 2.69±0.73 MPa and 6.30±1.26 MPa, respectively. Its ultimate tensile strength was 3.87±0.85 MPa. A typical polymeric stress-strain profile was observed when TN substrates were tested under tensile strain. The tensile modulus (0.79±0.18 MPa) of TN substrates was less compared to that of leaflets; however, their elongations were almost similar i.e. TN substrates in trilayered form were more elastomeric compared to leaflets. Ultimate tensile strength of TN substrates was also low (0.39±0.11 MPa). In heart valve tissue engineering, substrate with low mechanical properties is the prerequisite for the growth of VICs without their phenotype transformation from fibroblast or active myofibroblast to contractile or pathogenic myofibroblast.

Due to the non-conductive property of polymeric (PCL) nanofibers, the fibers hold charges even after deposition on a non-conductive area. Depositing fibers thus face the repulsion force from the deposited fibers due to their similar charges causing formation of lithe and highly porous nanofibrous layers in TN substrates. Beside high porosity, fibers orientations in the TN substrate were responsible for its low mechanical properties. When a load T is applied to a third of a TN substrate, it is applied to the fibers of each layer. In the circumferential layer, cosine components of T work for elongation of fibers while its sine components work for their straightening. Smaller nanofibers in this layer face more strain compared to longer nanofibers for the same load. Thus, elongation with straightening and then rupturing will occur in nanofibers starting from small to comparatively longer ones. As all the circumferentially oriented fibers will not take part equally together at any time, low amount of load will be required for the rupture of a circumferential layer. Load on a randomly oriented layer will be carried by all its fibers uniformly; however, the layer is also weak due to its high porosity. Nanofibers of a radially oriented layer will carry higher amount of load with decrease of γ angle and fibers are not connected to each other between dot and the periphery; thus, this layer carry least amount of load in circumferential direction compared to other two layers. Thus, fibers orientations and porosity caused low mechanical properties of TN substrates.

VICs harvested from porcine aortic valve leaflets were cultured in tissue culturing flask to obtain sufficient cells and then seeded and cultured in TN substrates statically in presence of ascorbic acid to produce trilayered constructs (TCs) with deposition of collagen fibrils, the main component of native leaflets. The seeding VICs had myofibroblast phenotype due to their culturing in a tissue culture flask—a substrate with high mechanical properties (stiffness: ~3 GP). After one month culturing, the constructs were characterized. VICs on both outer layers (circumferentially and radially oriented layers) of the growing constructs were stretched and spindle shaped and the cells were oriented along the nanofibers of respective layers. Their morphologies and orientations were comparable to those of VICs in fibrosa and ventricularis layers of native aortic valve leaflets. Instead of SEM images, immunostained images of native layers were useful to detect cells within numerous collagen fibrils. At higher magnification, we observed large numbers of aligned nanoscale collagen fibrils in circumferentially and radially oriented layers of the TCs. Similar aligned collagen fibrils were observed in fibrosa and ventricularis layers of a native leaflet. Collagen nature of these fibrils in TCs and native leaflets was confirmed by Masson's trichrome staining. Collagen fibril diameter (24±3.7 nm) in growing TCs was almost half of that (51±1.6 nm) in native leaflets.

Uniaxial tensile tests on the TCs were performed along the circumferential direction to determine their mechanical properties and compare them with that of native leaflets and TN substrates. Stress-strain profiles of the constructs were quite different from that of TN substrates; however, they were similar to that of native porcine leaflets—both containing two regions of moduli. First region of modulus can be caused by undulated arrangement of deposited collagen fibril in TN substrate as seen in the native leaflet. The moduli of construct at two regions were 1.20±0.36 MPa and 2.50±0.67 MPa, respectively, which were higher than that (0.79±0.18 MPa) of TN substrates. Ultimate tensile strength of TCs was 0.86±0.22 MPa. Thus, produced collagen, elastin and proteoglycans in TN substrates by VICs could be responsible not only for the transformation of the stress-strain profile of the single-region modulus to a profile of the two-region moduli but also for the increment of modulus and ultimate strength of TN substrates. With further growth of the construct, their mechanical properties could be close to that of native valve leaflets.

In the cross-sectional images of the constructs obtained through transmission electron microscopy (TEM), presence of proteoglycan and elastin including collagen were detected. Like in a native leaflet, three distinct layers (layers x, y and z separated by white lines) containing major proteins—collagen, collagen/proteoglycan and collagen/elastin, respectively, were formed in a TC. Shape, size and orientation of VICs in three layers of a TC were distinct due to diverse orientations of nanofibers present in those layers. In both the ventricularis layer of a leaflet and its equivalent radial layer of a TC, elastin bundles were present within the vast number of collagen fibrils. The spongiosa layer of a native leaflet and its equivalent random layer in a TC were less dense compared to the remaining two layers. Proteoglycans were distributed sporadically within collagen fibrils in the randomly oriented layer of a TC as found in the spongiosa layer of a native leaflet. Highly aligned collagen fibrils were in large number in the circumferentially oriented layer of a TC as observed in the fibrosa layer of a native leaflet. The size and thickness of collagen fibrils, proteoglycans and elastin bundles in a leaflet were larger than that in a TC because the later one was in developing stage. However, visually it seems that qualitative proportions of these ECM components in fibrosa, spongiosa and ventricularis layers of a leaflet and in their equivalent circumferentially, randomly and radially oriented layers in a TC were almost similar. Further, randomly and radially oriented layers of a TC showed collagen fibrils with transverse alignment as found in spongiosa and ventricularis layers of a native leaflet, respectively, in their cross-sectional images leading to conclusion that the orientations of collagen fibrils in all layers of a TC were similar to that in corresponding layers in a native leaflet.

In addition to structural and qualitative compatibility of collagen, proteoglycan and elastin in native aortic valve leaflets and in TCs, the relative quantities of these ECM components were almost equivalent. Collagen deposition in TCs was 1.593±0.105 µg/mg (in terms of hydroxyproline), compared to 1.747±0.094 µg/mg in native leaflets. Proteoglycan was 1.517±0.108 µg/mg in the constructs and 0.092±0.019 µg/mg in the leaflets. In a native leaflet, spongiosa holds ~25% of its thickness, whereas for a TC, it was ~33%. This increase in proportional thickness contributed higher amount of proteoglycan in TCs compared to that in native leaflets. Elastin deposition was 1.885±0.105 µg/mg in TCs and that in leaflets was 2.063±0.091 µg/mg. Due to similar proportionate thicknesses and presence of nanofibers in the radial direction, both the TC and native leaflet showed almost similar concentrations of elastin.

At the fetal developing and remodeling stages of heart valve leaflets, VICs show active myofibroblast phenotype, characterized by high gene expression of vimentin (fibroblasts) and α-smooth muscle actin (smooth muscle cells). VICs in both TCs and native leaflets showed high expression of vimentin. However, their α-SMA expression varied; this gene expression of VICs in TCs was almost two and half times of that in native leaflets. High α-SMA gene expression of VICs in TCs confirms their active myofibroblast phenotype; i.e., VICs in TCs were active for transforming the nanofibrous substrates into a trilayered leaflet constructs through their growth and deposition of various proteins. In case of valve disease, myofibroblasts produce fibrotic collagen causing the increase of leaflet stiffness and contraction. Further, phenotype of VICs changes from active/pathogenic myofibroblast phenotype toward osteoblast phenotype with passage of time, leading to calcification. However, we did not observe even the slightest contraction of very pliable TC produced after one month culturing of VICs in TN substrate statically. In contrary, same VICs showed contractility within ten days of their culture on a glass coverslip (stiffness: 72.4 GPa) leading to bending of coverslips despite similar expression of α-SMA, vimentin and COL1A1 by VICs both on coverslips and in TN substrates. This observation confirms that VICs in TN substrates were in developing mode. Further, expression of collagen gene COL1A1 by VICs in both native leaflets and TCs was almost similar which support the collagen quantification results.

To confirm the observed gene expression of VICs in native leaflets and TCs, we performed immunostaining of VICs with anti-vimentin and anti-α-SMA antibodies. VICs in TCs showed least α-SMA staining in circumferential layer and highest in radial layer. Nature and number of focal adhesion complexes (FACs) that depends mainly on morphology and mechanical properties of the nanofibers in each layer of a TN substrate was responsible for variation in α-SMA stress fiber formation. FACs on radial layers had more maturity compared to that on circumferential layers due to higher mechanical properties of individual nanofibers on earlier one. A video image can show α-SMA stained VICs and their orientations in a TC. Likewise, while no positive α-SMA staining was observed in fibrosa layer of a native leaflet, some staining was witnessed in its ventricularis layer. In general, VICs in healthy leaflet show quiescent fibroblast characterized by moderate vimentin expression and very low α-SMA gene expression. However, expressions of both vimentin and α-SMA in leaflets were comparatively higher than the general observation. The region close to the free edge of a leaflet showed positive staining anti-α-SMA antibody although most of the leaflet area did not show any α-SMA staining. The possible reason could be remodeling near the free edge of the leaflet in the ventricularis layer. Thus, the VICs near the free edge of a leaflet had myofibroblast phenotype confirmed by moderate α-SMA gene expression and staining. Vimentin-stained VICs were observed in both the TCs and native leaflets; these phenomena confirm their vimentin gene expression linked to fibroblast phenotype discussed before. VICs stained with vimentin in a TC can be seen in a video image. In both staining videos, the middle layer was found to be less dense compared to two remaining outer layers as observed in TEM images.

Previously, there were several attempts to develop a trilayered leaflet by several research groups; however, a biomimicked trilayered leaflet is yet to be produced in vitro. In this study, the efforts to produce a trilayered leaflet that mimicked a native leaflet structurally, morphologically and biologically was quite successful and it was possible only through static cell culturing. In the native leaflet development, the formation of oriented collagen fibrils, proteoglycans and elastin bundle occur due to presence of a dynamic environment. Thus, this study indicates that morphological influence of nanofibers may substitute the dynamic environment present in in vivo, in engineering of heart valve leaflets. Developmental mechanism of a native heart valve including its leaflets is very complex and not understood yet completely. However, it is known that alignment of cells and their deposited proteins in three layers of a native leaflet occur due to hemodynamic forces and its direction which could have been replaced by resilience and alignment of nanofibers in TN substrates, respectively, in this biomimicked leaflet development.

As this growing leaflet construct—the main and most complex component of a heart valve—showed positive development, a tissue engineered heart valve with trilayered leaflet can be produced in vitro by modifying the design of the TN substrate. Further, as the growing construct was completely standalone and made of PCL with cellular materials, it could be useful for studies of leaflet dysfunctionalities in vitro or in vivo. Development of native leaflets could be explored further with this trilayered structure.

Methods to Prepare a Biologic Trilayered Leaflet Construct

Fabrication of Electrospinning Collectors

An aluminum ring of inner diameter and outer diameter 1 and 1.05 inch, respectively and of thickness 0.04 inch was prepared from an aluminum plate. This ring was used to prepare randomly oriented nanofibrous layer. Two 24 gauge holes were made at opposite sides of ring periphery to hold the ring in front of spinneret using 24 gauge aluminum wire (Malin Co. USA) extended from a stand with the help of a clamp. To prepare radially oriented layers, another 24 gauge aluminum wire with a tiny sphere head at its end was extended from the stand to the middle of the ring. Equally spaced 24 holes with a diameter to fit the 24 gauge aluminum wire were made on an aluminum ring. Twelve aluminum spokes were made from 24 gauge aluminum wire and placed in the opposite holes of the aluminum ring to prepare metallic spoke-in-ring collector. This collector was hold by an alligator clip attached to the stand.

Fabrication of PCL Ring Frame

One side of metal ring that was used to prepare radially oriented nanofibrous layer was coated with biocompatible grease and then 18% (wt/v) polycaprolactone (PCL, MW: 80 KD, Sigma Aldrich, USA) solution in trifluoroethanol (Sigma Aldrich, USA) was poured on that side to make PCL ring frame attached to the metal ring. The thickness of the PCL ring frame was ~0.25 mm.

Fabrication of Trilayered Substrate

Metal ring with attached PCL ring and with an extended wire to the center of the ring was positioned in front of spinneret and was grounded. 9% (wt/v) polycaprolactone (PCL, MW: 80 KD, Sigma Aldrich, USA) solution in trifluoroethanol (Sigma Aldrich, USA) was electrospun at a discharge rate of 0.3 ml/hr, a gap-distance between spinneret needle and collector of 20 cm and a voltage-supply of 17 kV to produce PCL nanofibers with radial orientation. This radially oriented nanofibrous layer with PCL ring frame was removed from the collector and positioned on a metal ring to electrospin randomly oriented nanofibers over the radially oriented layers. The produced bilayer with PCL ring frame was then removed from the metal ring collector and placed on spoke-in-ring collector and electrospinning was performed. After producing a circumferentially oriented nanofibrous layer on the bilayered substrate, the trilayered nanofibrous (TN) substrate with PCL ring frame was removed from the collector. Final trilayered substrates were used for cell seeding or their characterizations.

Tensile Testing

Microscale tensile tester (Bose, USA) was used for uniaxial tensile testing of TN substrates, porcine aortic valve (PAV) leaflets and trilayered constructs. TN substrates and trilayered constructs were cut into pieces with ⅓ size of original sample to obtain a shape almost similar to the shape of a PAV leaflet. A test window frame made of hard paper with the window dimensions 11 mm×10 mm was used to hold the samples and prevent unwanted damage to the sample before testing. A sample was placed in a test window frame and glued to prepare a test sample. The test sample was placed in a tensile tester and was then loaded at the extension rate 0.1 mm/sec after cutting of the window frame along the cut line. A 150 gm load cell was used to sense the load on the sample until failure. The thickness of the samples was measured using optical microscope/TEM images. At least 3 samples of each type were used for tensile testing.

Cell Extraction and Culture

Aortic valve leaflets were aseptically collected from pig heart obtained from Hormel Foods (Austin, Minn., USA), washed in copious amount of sterile PBS and placed in trypsin (Invitrogen, USA) at 37° C. for 5 min. The leaflets were then swabbed gently to remove the endothelial layer from their surfaces and then digested in 0.5% (wt/v) type I collagenase (Worthington Biochemical, USA) in phosphate buffer saline (PBS, Hyclone, USA) at 37° C. for 5 hr. VICs were then isolated by centrifuging the digestion at 1000 rpm for 10 min and resuspended and expanded in tissue culture (TC) media from Dulbecco's modified Eagle's medium (DMEM, Corning, USA) supplemented with 10% fetal bovine serum (FBS, Atlas Biologicals, USA) and 1% penicillin-streptomycin (Life Technologies, USA) in tissue culture flasks.

Cell Seeding and Culture

The TN substrates were sterilized by incubating them in 70% ethanol for 1 hr at room temperature (25° C.) and then washing in copious amount of PBS in a sterile place. 1 million VICs in 2 ml TC media with ascorbic acid (150 µg/ml) (TC-A media) were seeded on TN samples. After first day of culture, TC-A media was replenished to remove the non-attached cells. The seeded cells in TN substrates were cultured in TC-A media for one month with replenishing of media every three days to produce trilayered constructs.

SEM Imaging

TN substrates, trilayered constructs and PAV leaflets were processed for SEM imaging. For cross-sectional imaging, the samples were place in OCT and then frozen for their transverse sectioning in a microtome. The section samples and whole samples were fixed in 4% formaldehyde overnight at 4° C. The samples were then rinsed in PBS, dehydrated in a graded ethanol series and dried in a critical point drier. Dried samples including TN substrates were sputter coated with gold-palladium at 18 mA for 20 s and imaged with scanning electron microscope (Hitachi, Japan) with EDX detector (Carl Zeiss, USA) at 15 kV.

TEM Imaging

Construct and PAV leaflet samples were fixed in a mixture of 2.5% glutaraldehyde and 4% formaldehyde in PBS for 2 hr, rinsed in PBS, fixed in 1% osmium tetroxide for 1 hr, washed in distilled water and then, dehydrated through graded ethanol. For epoxy resin infiltration, the samples were treated with ethanol-acetone mixture (1:1, by volume) for 10 m, acetone for 10 min, acetone-epoxy resin (2:1, by volume) for 30 min, acetone-epoxy resin (1:1, by volume) for 30 min, acetone-epoxy resin (1:2, by volume) for 30 min and epoxy resin overnight. The samples were then embedded in fresh epoxy resin and cured overnight at 60° C. The embedded samples were sectioned, collected on copper grids and imaged with transmission electron microscopy (Jeol, Japan).

Protein Quantification

For collagen and glycosaminoglycan (GAG) quantifications, construct and PAV leaflet samples were rinsed in PBS and lyophilized. Their weights were measured and then, they were digested in papainase buffer containing papain type III (Worthington Biochemical, USA). Supernatants were collected by centrifugation for collagen and GAG quantifications. Collagen quantifications were performed according to manufacturer protocol (Sigma, USA). In brief, 100 µl of the papain digest was added to 100 µl of 12N HCl and hydrolyzed at 120° C. for 3 h. 50 µl of the hydrolyzed sample was transferred to 96-well plate and dried at 60° C. 100 µl chloramine T/oxidation buffer mixture (94:6) was added to the dried sample and incubated at room temp for 5 min. 100 µl of diluted DAMB reagent was added to the sample and incubated at 60° C. for 90 min. After cooling the samples to room temperature, their absorbance at 557 nm were recorded and compared with standard curve obtained by measuring the absorbance of known hydroxyproline solution.

GAG quantifications were performed according to manufacturer protocol (Blyscan, Biocolor, USA). 50 µl DI water was added to 50 µl of the papain digest prepared before and then 1 ml GAG dye was added to the solution. The dye mixed solution was placed in a shaker for 30 min and then centrifuged at 12000 rpm for 10 min. after removing the supernatant, the precipitate was dissociated with 0.5 ml dissociation agent. The sample was analyzed at 656 nm absorbance and compared with standard curve obtained by measuring the absorbance of known GAG standard solutions.

Elastin quantification was performed according to company protocol (Fastin, Biocolor, USA). Construct and PAV leaflet samples were rinsed in PBS and lyophilized. Their weights were measured and then, they were incubated in 0.25M oxalic acid at 100° C. for 1 hr. After centrifuging, the supernatant was added to elastin precipitate agent and the precipitate was dyed with dying agent through complete mixing. Through centrifuging, dyed elation was collected as precipitate and then dissociate with dissociating agent. The sample was then analyzed at 513 nm absorbance and compared with standard curve obtained by measuring the absorbance of known elastin standard solutions.

Gene Expression Analysis

RNA from construct and PAV leaflet samples was extracted using Pure Link RNA mini kit (Ambion, Life Technologies, USA) according to manufacturer's protocol. The extracted RNA was purified with DNase I (Life technologies, USA) according to manufacturer's protocol. First-strand cDNA was synthesized from purified RNA using High-Capacity cDNA Reverse Transcription kit with RNase Inhibitor (Applied Biosystems, USA). cDNA transcripts were then probed with TaqMan assays for vimentin (Ss04330801_gH), α-smooth muscle actin (α-SMA, Ss04245588_m1), and type I collagen (COL1A1, Ss03373341_g1) using Lightcycler 480 Probe master mix (Roche, USA). Thermocycling was performed in a Lightcycler 480 (Roche Applied Science, USA) with the following conditions: pre-incubation (95° C., 15 min), 40 cycles of amplification (denaturation: 95° C., 15 s; annealing: 60° C., 1 min; and extension: 72° C., 1 s) and cooling (40° C., 30 s). Target gene data were normalized against ACTB level and analyzed using the comparative cycle threshold (Ct) method.

Masson's Trichrome Staining

Fibrosa and ventricularis layer sections were cut from frozen PAV leaflet tissue samples with OCT in a microtome. Tissue sections and construct samples were fixed in 4% formaldehyde overnight at 4° C. The samples were then rinsed in PBS and then stained with Masson's trichrome using manufacturer's instruction (Sigma Aldrich, USA). The samples were then rinsed, dehydrated, mounted on glass slides using a mounting media and imaged in an optical microscope.

Immunostaining

Fibrosa, spongiosa and ventricularis layer sections were cut from frozen PAV leaflet tissue samples with OCT in a microtome. Tissue sections and construct samples were fixed in 4% methanol-free formaldehyde overnight at 4° C. The samples were washed in PBS, incubated in 0.1% Triton X-100 for 2 min, washed in PBS, and incubated in 10% goat serum for 30 min. The samples were then incubated in a mouse anti-vimentin IgM primary antibody (Novus Biologicals, USA) at a 1:500 dilution in PBS for 1 hr. They were then washed in PBS and incubated in AF 488 conjugated goat anti-mouse IgM secondary antibody (Abcam, USA) at 1:500 dilution in PBS for 45 min. The samples were then washed in PBS and mounted on glass slide using Prolong Gold Antifade reagent with DAPI (Invitrogen) mounting media. For smooth muscle actin staining, primary and secondary antibodies were mouse anti-human smooth muscle actin IgG (Dako, USA) and AF 594 conjugated goat anti-mouse IgG (Abcam, USA).

Example #2

A circumferentially oriented nanofibrous substrate mimicking the structure of fibrosa layer of an aortic valve was developed. VIC-cultured nanofibrous substrate demonstrated gene and protein expression and morphology that mimic fibrosa layer of a native aortic leaflet. In addition to comparable structural and biological properties of the developed prototype with native fibrosa layer, this prototype is made of PCL which is a FDA approved biodegradable material; thus, the prototype can be used both in vitro and in vivo studies and with time, PCL nanofibers will be replaced by depositing collagen fibrils from VICs. Applying VICs from human sources, this novel fibrosa layer might be the basis for bioengineered hearts.

We have developed a pliable but standalone CON substrate comprising circumferentially oriented nanofibers. CON substrates had much higher pore size compared to those general substrates. Due to the non-conductive property of deposited polymeric (PCL) nanofibers in electrospinning system, the fibers hold charge. In our spokes-in-ring collector, only two ends of nanofibers were attached to adjacent spokes and thus, fibers between two adjacent spokes carried similar charges causing repulsion among them leading to high porosity in CON substrate. Unlike CON substrate, nanofibers in RON substrate were compact owing to presence of metallic plate at the back of ring collector while electrospinning; however, we prepared a thin RON substrate so that cells can spread into the substrate.

High porosity contributed low bulk tensile modulus to CON substrates. Beside high porosity, circumferential orientation of fibers in a CON substrate was responsible for its low bulk mechanical properties. A third of a CON substrate has almost equivalent shape and circumferential orientation of a fibrosa layer in a PAV leaflet. When a tensile load T is applied to this leaflet-shaped CON substrate, circumferentially oriented nanofibers across the substrate bear the load. One component of T (cosine of T)—tangent to nanofibers will be responsible for elongating the fibers and another component of T (sine of T)—perpendicular to nanofibers will be responsible for straightening the fibers. With this low force (T cos α or T cos β<T), fibers will elongate slowly—first elongation of small polymer chains and then comparatively longer polymer chains in the fibers; thus, the fibers will have high elongation. At higher tensile load, small polymer chains will have less chance to resist the load compared to their longer counterparts and thus, less elongation of fibers will take place, i.e. high stiffness will be observed. The stiffness of PCL nanofibrous substrate was 22.08±5.19 MPa when the aligned fibers in the substrate were straight.

Further, lengths of all the circumferentially oriented nanofibers across the substrate are not similar and shorter nanofibers will face the more strain compared to longer ones for the same load. Thus, straightening with elongation and then rupture will occur to the shorter nanofibers first and will propagate towards comparatively longer nanofibers. As all fibers don't work together equally at any time against the load, low amount of load will be required to rupture the whole sample and thus, CON substrates showed low stiffness and strength with high elongation. In this schematic image of a leaflet-shaped CON substrate, only fibers within two consecutive spokes have been considered to keep the analysis simple; however, for fibers with more spokes, similar explanation can be adopted. Fibers at different fiber-spoke junctions will face equivalent force components but at different directions. Thus, not only fibers within same consecutive spokes will face varied strain but also fibers within different consecutive spokes will face varied strain. Seeded VICs will witness similar force resolutions when they will stretch themselves during their growth. In case of RON substrates, the fibers were randomly oriented and can be considered homogeneous in the tensile testing plane. So, all the fibers in a RON substrate will resist together uniformly at any time point of tensile testing. Due to compactness of fibers in RON substrates, the substrates showed higher mechanical properties compared to CON substrates.

Cells on CON substrates were circumferentially oriented due to guidance form the oriented nanofibers and thus, produced collagen fibrils were oriented. Any defined orientation of collagen fibrils was not observed on RON and WPD substrates for the same reason. Due to low bulk mechanical properties of CON substrates, VICs demonstrated active fibroblast phenotype (high vimentin, high collagen type I and low α-SMA expression). CON substrates could have been in developing state or could have reached to fully grown state and that is why, their α-SMA expression was comparatively higher than that of native leaflets. However, same VICs were found to have myofibroblast phenotype on a substrate (hydrogel, a non-fibrous substrate) with modulus as low as 15 kPa. Nanofibrous morphology of CON substrates could be responsible for its fibroblast phenotype. VICs on higher modulus RON substrates (6.37±2.03 MPa) compared to CON substrates had active myofibroblast phenotype that could lead to contractile myofibroblast phenotype with the passage of time. Thus, this study can bring forth an apparent but important conclusion that although phenotype of VICs depends mainly on mechanical properties of substrates, the morphology of substrates may influence it.

Nature of generated focal adhesions (FAs) formed between the VICs and the underlying substrates may explain the behavior and the phenotype expression of the cells. The growth, size, maturity and number of FAs depend on morphology, mechanical and biophysiochemical properties of substrates. It is reported that number of FA on a planar surface is more than on the substrates made of nanofibers. Substrates with high mechanical properties shows the presence of large size supermature FAs (SuFAs) that allow incorporation of α-SMA into preexisting cytoplasmic actin stress fibers leading to myofibroblastic phenotype of fibroblasts. The generated force by α-SMA actin stress fibers is much higher than the force from cytoplasmic actin stress fibers and thus, can cause contraction if myofibroblastic phenotype continues after tissue development or remodeling. FAs on a substrate with less mechanical properties are less mature and smaller in size, and in them, α-SMA doesn't get into cytoplasmic actin stress fibers. This state could be represented by active fibroblast phenotype. More cell-cell contacts on a substrate are in favor of fibroblast phenotype.

VICs on a hydrogel substrate of stiffness <8 kPa showed fibroblast phenotype and on a similar hydrogel substrate of stiffness ~15 kPa showed myofibroblast phenotype. So, for that hydrogels, there should be threshold stiffness in between 8 and 15 kPa for FAs of VICs to achieve supermaturity. However, VICs on CON substrate (stiffness: 330 kPa) did not show α-SMA stress fibers. Number of FA (generally 4 for each cell) on CON substrate was negligible compared to that on flat surface. Further, cell-cell contacts on CON substrate were substantial and these parameters might have been conducive for VICs on CON substrate to express active fibroblast phenotype. RON substrate had higher stiffness, higher number of FAs for each cell and less cell-cell contact compared to those on CON substrate and thus, VICs on RON substrate showed myofibroblast phenotype. On WPD substrate with very high stiffness, VICs had numerous FAs, very few cell-cell contacts and thus, VICs on WPD substrate expressed contractile myofibroblast phenotype.

Due to positive phenotype of VICs, their deposited type I collagen fibrils on CON substrates were as smooth as native collagen fibrils. The substrate is also pliable like leaflet of a heart valve. Further, the nanofibers were circumferentially oriented—thus, the VICs were provided a biomimicked microenvironment in the CON substrate. In contrast, VICs had active myofibroblast phenotype with random cell orientation and less deposition of type I collage; thus, RON substrates could not mimic the fibrosa layer. WPD substrates were not useful at all in producing either artificial leaflet or any of its layers as VICs showed highly active myofibroblast phenotype due to flat surface and high mechanical properties of WPD substrates with no guidance to the cells. WPD substrates i.e. tissue culture well plates, thus were found not appropriate in VIC culturing for valve dysfunction study. Therefore, it can be concluded that VIC-cultured biomimicked CON substrates could represent fibrosa layer in terms of morphology and molecular signature. A limitation of this study is that gene expression and protein quantification of CON, RON and WPD samples were compared with those of whole native leaflet instead of its fibrosa layer.

Fabrication of Substrates and their Characterizations

Among techniques including phase separation and self-assembly, electrospinning is the most commonly used to prepare nanofibrous substrates due to its versatility, applicability to most polymers, easy handling and cost-effectiveness. In this technique, orientation of the deposited fibers depends on the fiber-collector design. Fabrication process of a model fibrosa layer consists of several steps shown in FIG. 1. We first designed a novel spokes-in-ring collector (FIG. 11) to fabricate circumferentially oriented nanofiber. A ~0.25 mm-thick PCL ring-frame was made on one side of ring periphery of the collector by pouring 18 wt % PCL solution. We then produced circumferentially oriented nanofibrous (CON) substrate by electrospinning 9 wt % polycaprolactone (PCL) solution on the collector. Between the spokes, a magnetic field was formed that pulled one end of a nanofiber towards one spoke and another end towards the adjacent spoke perpendicularly and thus deposited fibers were concentric. Polycaprolactone was selected because it is easy to spin, has slow biodegradation property and can be applied for in vivo study. The developed substrates have a spokes-in-ring shape with circumferentially oriented PCL nanofibers connected to adjacent nanofibrous spokes (FIGS. 13 and 14). Nanofibrous membrane with PCL ring-frame at its periphery came out easily from the collector. Unlike other generally used nanofibrous substrates in tissue engineering, our developed CON substrates do not require structural support such as glass coverslip at their back due to presence of PCL ring-frame at their peripheries, so these substrates are fully standalone (FIGS. 15 and 16). Presence of glass coverslip (stiffness: 72.4 GPa) will certainly change the phenotype of VICs from fibroblast to pathogenic myofibroblast which is not desirable at all. Further, the CON substrates are pliable like a native leaflet (FIGS. 17-19). We hypothesized that this CON substrate can be a prototype of a native fibrosa layer after culturing the substrate with VICs. On an aluminum ring with PCL ring-frame on it (FIG. 7), we prepared randomly oriented nanofibrous (RON) substrate as a control substrate (FIG. 9). A metal plate was placed at the back of the ring to produce random nanofibers in the inner space of the ring. Discs (polystyrene well plate disc, WPD) with diameters similar to CON or RON substrate were cut from the wells of 6-well tissue culture plates to serve as another control. Comparisons of substrates and their VIC-cultured counterparts were made with freshly isolated porcine aortic valve (PAV) leaflets.

Structure of collectors influences the porosity of substrates and CON substrate had much higher porosity compared to RON. Fiber diameter of both CON and RON substrates scanned in electron microscopy was 370±73 nm. For tensile test, a third of CON and RON substrates with shape equivalent to the shape of a PAV leaflet were considered as test sample. The uniaxial bulk tensile moduli of CON, RON, WPD substrates and aortic valve leaflet were 0.33±0.19 MPa, 3.82±1.03 MPa, ~3 GPa and 7.25±2.10 MPa, respectively and their ultimate strengths were 0.14±0.06 MPa, 1.21±0.39 MPa, ~40 MPa and 1.83±0.64 MPa, respectively.

Morphology of Seeded Cells

VICs harvested from PAV leaflets were seeded on CON, RON and WPD substrates and cultured for one month in presence of ascorbic acid which was used to induce the deposition of collagen—the main component of a native leaflet. The proliferation of VICs was the highest on CON substrate and lowest on WPD substrate (FIG. 3a), which confirms that nanofibrous substrate supports proliferation of VICs and oriented nanofibers favor higher VICs proliferation. After one month of culturing, VICs on the CON substrates were found to be stretched, smoothly flat, and aligned concentrically with almost no empty space between the adjacent cells (FIG. 3b), whereas the same VICs on RON substrates were less stretched, more irregular, and randomly oriented with empty space between the adjacent cells (FIG. 3c). VICs on the WPD substrates were spindle shaped and were radially oriented sporadically. Very few cells were stretched and there were many gaps between these cells on the WPD substrates. Both morphologies and mechanical properties of the substrates played crucial roles in determining the behaviors of VICs—their shapes, orientation and cell-to-cell connectivity. Due to porosity and stand-alone structure of the nanofibrous substrates, cells were present at both sides of CON and RON substrates only.

Characterization of Deposited Collagen Fibrils

Deposition of collagen fibrils from VICs on each type of substrate was also observed. The fibrils on CON substrates were mostly aligned similar to aligned collagen fibrils in a native fibrosa layer, whereas they were no alignments on RON substrates. On WPD substrates, the fibrils were sparsely aligned. Masson's trichrome staining confirmed the collagen nature of fibrils. From the top surface, more than one cell layer with different cell orientations are visible only on WPD substrates. Similarly, CON and RON substrates had layers of VICs throughout the substrates. The diameters of collagen fibrils on all substrates were almost half of those in a native aortic fibrosa layer (50±0.834 nm) and their diameters on CON, RON and WPD substrates were 25.6±0.9, 24.1±0.7, 22.6±0.3 nm, respectively. Transmission electron microscopy (TEM) images of these collagen fibrils show the band periodicities confirming type I collagen; however, among the substrates, periodicity in collagen fibrils was most and least distinct on CON and WPD substrates, respectively.

Cross-section images obtained through TEM exhibit higher number of cell layers with collagen fibrils between the layers of cells on CON and RON substrates than on WPD substrates. Number of layers depended on the thickness of the CON or RON substrates. However, with less cell layers and the lowest fibril diameter, WPD substrates were found to have the highest amount of collagen deposition (2.76±0.34 μg of hydroxyproline/mg). CON, RON substrates and leaflets had collagen deposition (in terms of hydroxyproline) of 1.73±0.25 μg/mg, 0.23±0.03 μg/mg and 1.81±0.21 μg/mg, respectively. Higher mechanical properties of WPD substrates were responsible for lower fibril diameter and higher fibril density and this could lead to higher collagen deposition on WPD substrates.

At higher magnification, the collagen fibrils on CON and RON substrates were found to be very smooth, similar to the collagen fibrils in fibrosa layer of leaflets. In contrast, collagen fibrils on WPD substrates revealed a large number of tiny nodules (size <30 nm) on them. However, in their energy dispersive X-ray (EDX) spectrum, no traces of calcium, sodium and phosphorous—the elements that exist in hydroxyapatite mineral, were observed on all substrates (data not provided). Further, no positive staining was observed in any of the substrate samples in the Alizarin Red S staining assay (ARS, for calcium staining), (data not provided). TEM imaging also did not show any evidence of electron-dense mineral deposits.

Gene Expression and Immunostaining Analysis

VICs may assume various phenotypes including those of native quiescent fibroblasts, active fibroblasts, active myofibroblasts and osteoblasts in aortic valve leaflets depending on their surrounding environment and valve status. Quantitative gene expression of these phenotypes is listed in Table S1. We quantified gene expression from VICs on different substrates and from the PAV leaflets. VICs on RON substrates had low expression of vimentin and COL1A1, and high expression of α-SMA which signifies VICs on RON substrates were similar to active myofibroblast phenotype. Also, collagen deposition on this substrate was low. In contrast, VICs on CON substrates had lower expression of α-SMA but higher expression of both vimentin and COL1A1 compared to that on RON substrates and thus, their phenotypes could be consistent with active fibroblasts. This lead to the formation of a model fibrosa layer with increased collagen type I deposition on the CON substrate. VICs in PAV leaflets had little higher expressions of VIM and COL1A1 and lower expression of α-SMA compared to that on CON substrates. Consequently, the phenotype of VICs in PAV leaflets could be active fibroblast. Free edge of PAV leaflets are subjected to dynamic remodeling and can cause the fibroblast be active showing α-SMA expression. On WPD substrates, VICs had higher expressions of all genes and thus, they represented highly active myofibroblast phenotype, which is associated with contraction of leaflets, fibrotic stiffening and calcification in the leaflets through their differentiation towards osteoblast-like cells unless the substrate/leaflet is in development stage. To study contraction, we cultured VICs on polystyrene coverslips and within 10 days of culturing, contraction of VICs made all the coverslips bend whereas fewer RON and almost no CON substrates were found to have any contraction from VICs after 30 days of culturing. This contraction study on much stronger coverslip compared to CON or RON substrate proved that VICs on WPD substrates were beyond development stage. The VICs on WPD substrates had higher expression of COL1A1 compared to VICs on other substrates, coinciding with higher collagen fibril deposition on WPD substrates.

To further confirm protein expression qualitatively, we immunostained the VICs from substrates and native PAV leaflets. VICs on all substrates demonstrated vimentin expression while their α-SMA expression varied. VICs on CON substrates had almost no α-SMA staining, whereas there was presence of α-SMA positive smooth muscle stress fibers on RON substrates. Although most of the VICs in leaflets did not express α-SMA, the VICs at the free edge showed α-SMA immunoreactivity. This positive α-SMA staining confirms the α-SMA expression in PAV leaflets. VICs on WPD substrates expressed α-SMA throughout the constructs.

Characterization of Elastin Deposition

In addition to collagen type I, we quantified the elastin deposition by VICs on CON, RON and WPD substrates, and compared them with those obtained from PAV leaflets. Elastin deposition on WPD substrates (56.98±8.04 μg/mg) was greater than that on CON substrates (46.26±7.11 μg/mg), RON substrates (34.12±4.13 μg/mg) and in leaflets (44.15±6.27 μg/mg). Higher mechanical properties of the WPD substrates, and especially radial orientation of VICs on that substrate, could be responsible for this higher elastin deposition. In TEM images of leaflets, CON, RON and WPD substrates, generated elastin can be seen.

Evaluation of the Model Fibrosa Layer

In order to evaluate the efficacy of the model fibrosa layer in valve dysfunctional study, one month VIC-cultured CON, RON and WPD substrates were cultured in standard DMEM media supplemented with 1 ng/ml TGF-β—a profibrotic growth factor, for ten days to induce calcification. The samples were then stained with alizarin red S (for calcium staining) to verify any calcification. Visual examination of the stained samples revealed that WPD substrate was the most susceptible to calcification and CON substrate was the least. This observation proves that the model fibrosa layer had healthy VICs with fibroblast phenotype that exists in the fibrosa layer of a native leaflet.

Methods to Prepare a Biologic Fibrosa Layer of a Native Aortic Leaflet

Fabrication of Electrospinning Collector

An aluminum ring of inner diameter and outer diameter 1 and 1.05 inch, respectively and of thickness 0.04 inch was prepared from aluminum plate. The ring contained equally space 24 holes that can fit aluminum wire of 24 gauge (Malin Co. USA). Twelve aluminum spokes were made from aluminum wire and placed in the opposite holes of the aluminum ring to prepare metallic spoke-in-ring collector. Without spokes, the collector was called ring collector.

Fabrication of PCL Ring-Frame

One side of metal ring intended to prepare circumferentially or randomly oriented nanofibrous layer was coated with biocompatible grease and then 18% (wt/v) polycaprolactone (PCL, MW: 80 KD, Sigma Aldrich, USA) solution in trifluoroethanol (Sigma Aldrich, USA) was poured on that side to make PCL ring-frame attached to the metal ring. The thickness of the PCL ring-frame was ~0.25 mm.

Fabrication of Substrate

9% (wt/v) polycaprolactone (PCL, MW: 80 KD, Sigma Aldrich, USA) solution in trifluoroethanol (Sigma Aldrich, USA) was electrospun at a discharge rate of 0.3 ml/hr, at a gap distance between spinneret needle and collector of 22 cm and at a voltage supply of 16 kV to produce PCL nanofibers. An aluminum spoke-in-ring collector was used as collector to fabricate concentrically oriented nanofibrous (CON) substrates. The ring without spokes was placed on metal plate to produce randomly oriented nanofibrous (RON) substrates. One side of the collectors was coated with a layer of PCL before electrospinning so that nanofibrous structures can work as standalone substrates individually after being detached from the collectors. 1 inch disc cut from bottom of wells of polystyrene 6-well tissue culture plate was used as another type of control substrate (WPD substrate).

Tensile Testing

Microscale tensile tester (Bose Electroforce, USA) was used for uniaxial tensile testing of both aligned and randomly oriented substrates. A third of a sample was sandwiched between two paper window frames with window dimension 11 mm×10 mm to prepare test sample. Straight aligned nanofibers were electrospun between two parallel metal plates, collected and then sandwiched between two paper window frames. Test samples were loaded at the extension rate 0.1 mm/sec. A 150 gm. load cell was used to sense the load on samples until failure. The thickness of the samples was measured using their SEM images. The tensile properties of WPD substrate were obtained from reported data in literature.

Cell Extraction and Culture

Aortic valve leaflets were aseptically collected from pig heart obtained from Hormel Foods (Austin, Minn., USA), washed in copious amount of sterile PBS and placed in trypsin (Invitrogen, USA) at 37° C. for 5 min. The leaflets were then swabbed gently to remove the endothelial layer from their surfaces and then digested in 0.5% (wt/v) type I collagenase (Worthington Biochemical, USA) in PBS at 37° C. for 5 hr. VICs were then isolated by centrifuging the digestion at 1000 rpm for 10 min and resuspended and expanded in tissue culture (TC) media from Dulbecco's modified Eagle's medium (DMEM, Corning, USA) supplemented with 10% fetal bovine serum (FBS, Atlas Biologicals, USA) and 1% penicillin-streptomycin (Life Technologies, USA).

Cell Seeding and Culture

The CON, RON and WPD substrates were sterilized by incubating them in 70% ethanol for 1 hr at room temperature (25° C.) and then washing in copious amount of phosphate buffer saline (PBS, Hyclone, USA) in sterile place. 1 million VICs in 2 ml TC media with ascorbic acid (150 μg/ml) (TC-A media) were seeded on nanofibrous samples. After first day of culture, number of cells attached to nanofibers in each of CON and RON substrates was close to 100,000. 100,000 VICs were seeded on the WPD substrate. The seeded cells on those substrates were cultured in TC-A media for one month with replenishing of media every three days. To induce calcification, one-month VIC-cultured substrates were cultured in standard DMEM media supplemented with 1 ng/ml TGF-β for seven days.

Cell Proliferation Study

AlamarBlue (AB, Invitrogen, USA) calorimetric assay was used to study the VIC proliferation on three types of substrates with passage of time following the company protocol. Briefly, samples were washed in PBS and incubated in 10% AB solution in TC media in a tissue culture incubator. 200 μl of assay solution was transferred to a 96-well plate in triplicate and measured at 560 nm (absorbance) in a spectrophotometer (SpectraMax Plus 384, Molecular Devices, USA). The measured absorbance data were transformed to cell numbers using a calibrated curve produced from the absorbance data of known cell numbers. Cell numbers were counted at 1, 3, 11 and 21-day time points.

SEM Imaging

Transverse and Fibrosa layer sections were cut from frozen PAV leaflet tissue samples in OCT in a microtome. Tissue sections and cultured samples were fixed in 4% formaldehyde overnight at 4° C. The samples were then rinsed in PBS, dehydrated in a graded ethanol series and dried in critical point drier. Dried samples including plain substrates were sputter coated with gold-palladium at 18 mA for 20 s and imaged with scanning electron microscope (Hitachi, Japan) with EDX detector (Carl Zeiss, USA).

TEM Imaging

Samples were fixed in a mixture of 2.5% glutaraldehyde and 4% formaldehyde in PBS for 2 hr, rinsed in PBS, fixed in 1% osmium tetroxide for 1 hr, washed in distilled water and then, dehydrated through graded ethanol. For epoxy resin infiltration, the samples were treated with ethanol-acetone mixture (1:1, by volume) for 10 m, acetone for 10 min, acetone-epoxy resin (2:1, by volume) for 30 min, acetone-epoxy resin (1:1, by volume) for 30 min, acetone-epoxy resin (1:2, by volume) for 30 min and epoxy resin overnight. The samples were then embedded in fresh epoxy resin and cured overnight at 60° C. The embedded samples were sectioned, collected on copper grid and imaged with transmission electron microscopy (Jeol, Japan).

Proteins Quantification

For collagen quantifications, cultures and leaflet samples were rinsed in PBS and lyophilized. Their weights were measured and then, they were digested in papainase buffer containing papain type III (Worthington Biochemical, USA). Supernatants were collected by centrifugation for collagen quantifications. Collagen quantifications were performed according to manufacturer protocol (Sigma, USA). In brief, 100 μl of the papain digest was added to 100 μl of 12N HCl and hydrolyzed at 120° C. for 3 h. 50 μl of the hydrolyzed sample was transferred to 96-well plate and dried at 60° C. 100 μl chloramine T/oxidation buffer mixture (94:6) was added to the dried sample and incubated at room temp for 5 min. 100 μl of diluted DAMB reagent was added to the sample and incubated at 60° C. for 90 min. After cooling the samples to room temperature, their absorbance at 557 nm were recorded and compared with standard curve obtained by measuring the absorbance of known hydroxyproline solution.

Elastin quantification was performed according to company protocol (Fastin, Biocolor, USA). Cultures and leaflet samples were rinsed in PBS and lyophilized. Their weights were measured and then, they were incubated in 0.25M oxalic acid at 100° C. for 1 hr. After centrifuging, the supernatant was added to elastin precipitate agent and the precipitate was dyed with dying agent through complete mixing. Through centrifuging, dyed elation was collected as precipitate and then dissociate with dissociating agent. The sample was then analyzed at 513 nm absorbance and compared with standard curve obtained by measuring the absorbance of known elastin standard solutions.

Gene Expression Analysis

RNA from cultured samples and leaflet samples was extracted using Pure Link RNA mini kit (Ambion, Life Technologies, USA) according to manufacturer's protocol with little modification. The cultured samples were washed with PBS, snap freezed in liquid nitrogen and kept at −80° C. until all the samples were collected. The frozen samples were homogenized in lysis buffer instantly without thawing. The homogenized solutions were processed according to protocol to extract RNA. The extracted RNA was purified with DNase I (Life technologies, USA) according to manufacturer's protocol. First-strand cDNA was synthesized from purified RNA using High-Capacity cDNA Reverse Transcription kit with RNase Inhibitor (Applied Biosystems, USA). cDNA transcripts were then probed with TaqMan assays for vimentin (Ss04330801_gH), α-smooth muscle actin (α-SMA, Ss04245588_m1), and type I collagen (COL1A1, Ss03373341_g1) using Lightcycler 480 Probe master mix (Roche, USA). Thermocycling was performed in a Lightcycler 480 (Roche Applied Science, USA) with the following conditions: pre-incubation (95° C., 15 min), 40 cycles of amplification (denaturation: 95° C., 15 s; annealing: 60° C., 1 min; and extension: 72° C., 1 s) and cooling (40° C., 30 s). Target gene data were normalized against ACTB level and analyzed using the comparative cycle threshold (Ct) method.

Masson's Trichrome Staining

Fibrosa layer sections were cut from frozen PAV leaflet tissue samples in OCT in a microtome. Tissue sections and cultured samples were fixed in 4% formaldehyde overnight at 4° C. The samples were then rinsed in PBS and then stained with Masson's trichrome using manufacturer's instruction (Sigma Aldrich, USA). The samples were then rinsed, dehydrated, mounted on glass slides using a mounting media and imaged in an optical microscope.

Alizarin Staining

Fibrosa layer sections were cut from frozen PAV leaflet tissue samples in OCT in a microtome. Tissue sections and cultured samples were fixed in 4% formaldehyde overnight at 4° C. They were then treated with 2 wt/v % alizarin Red S (Sigma Aldrich, USA) solution (pH 4.1-4.3) for 10 min, washed with DI water and then views in an optical microscope.

Immunostaining

Fibrosa layer sections were cut from frozen PAV leaflet tissue samples in OCT in a microtome. Tissue sections and cultured samples were fixed in 4% methanol-free formaldehyde overnight at 4° C. The samples were washed in PBS, incubated in 0.1% Triton X-100 for 2 min, washed in PBS, and incubated in 10% goat serum for 30 min. The samples were then incubated in a mouse anti-vimentin IgM primary antibody (Novus Biologicals, USA) at a 1:500 dilution in PBS for 1 hr. They were then washed in PBS and incubated in AF 488 conjugated goat anti-mouse IgM secondary antibody (Abcam, USA) at 1:500 dilution in PBS for 45 min. The samples were then washed in PBS and mounted on glass slide using Prolong Gold Antifade reagent with DAPI (Invitrogen) mounting media. For smooth muscle actin staining, primary and secondary antibodies were mouse anti-human smooth muscle actin IgG (Dako, USA) and AF 594 conjugated goat anti-mouse IgG (Abcam, USA).

Statistical Analysis

Data are reported as mean±standard deviation (SD). For data analysis, they are compared using ANOVA for statistical significance.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A biologic heart valve leaflet comprising a synthetic trilayered nanofibrous substrate material that comprises:
    a first layer comprising a radially oriented nanofibrous substrate comprising nanofibers extending between an exterior perimeter of the radially oriented nanofibrous substrate and a location within the exterior perimeter of the radially oriented nanofibrous substrate;
    a second layer comprising a randomly oriented nanofibrous substrate comprising nanofibers extending randomly within an exterior perimeter of the randomly orientated nanofibrous substrate; and
    a third layer comprising a circumferentially oriented nanofibrous substrate comprising nanofibers extending circumferentially around a location within an exterior perimeter of the circumferentially orientated nanofibrous substrate,
    wherein the second layer is disposed on a surface of the first layer, and the third layer is disposed on a surface of the second layer.

2. The biologic heart valve leaflet of claim 1, wherein the first layer, the second layer, and the third layer are each made using an electrospinning process.

3. The biologic heart valve leaflet of claim 1, wherein the second layer is disposed on the surface of the first layer by electrospinning the second layer onto the surface of the first layer.

4. The biologic heart valve leaflet of claim 3, wherein the third layer is disposed on the surface of the second layer by electrospinning the third layer onto the surface of the second layer.

5. The biologic heart valve leaflet of claim 1, wherein the first layer, the second layer, and the third layer comprise nanofibers having diameters in a range from about 100 nm to about 2 µm.

6. The biologic heart valve leaflet of claim 1, wherein the nanofibers comprise one or more from the group consisting of polycaprolactone, polyglycerol sebacate, polyglycolic acid, collagen, and poly(lactide-co-glycolide).

7. The biologic heart valve leaflet of claim 1, further comprising at least one of valvular interstitial cells, fibroblasts, and mesenchymal stem cells.

8. The biologic heart valve leaflet of claim 1, further comprising human valvular interstitial cells.

9. The biologic heart valve leaflet of claim 7, further comprising one or more polypeptides produced by the valvular interstitial cells.

10. The biologic heart valve leaflet of claim 9, wherein the one or more polypeptides comprise one or more of types of collagen, collagen/proteoglycan, and elastin.

11. A synthetic material that mimics a fibrosa layer of a native heart valve leaflet, the material comprising a substrate of electrospun circumferentially oriented nanofibers.

12. The material of claim 11, wherein the nanofibers have diameters of about 340+/−87 nm.

13. The material of claim 11, wherein the nanofibers comprise one or more from the group consisting of polycaprolactone, polyglycerol sebacate, polyglycolic acid, collagen, and poly(lactide-co-glycolide).

14. The material of claim 11, further comprising one or more of valvular interstitial cells, fibroblasts, and mesenchymal stem cells.

15. The material of claim 11, further comprising valvular interstitial cells, wherein the valvular interstitial cells are porcine or human valvular interstitial cells.

16. The material of claim 14, further comprising one or more polypeptides produced by the valvular interstitial cells.

17. The material of claim 16, wherein the one or more polypeptides comprise one or more types of collagen, proteoglycan, and elastin.

* * * * *